(12) United States Patent
Hemminghaus et al.

(10) Patent No.: US 10,212,933 B2
(45) Date of Patent: *Feb. 26, 2019

(54) LOW VOLATILITY HERBICIDAL COMPOSITIONS

(71) Applicant: Monsanto Technology LLC, St. Louis, MO (US)

(72) Inventors: John W. Hemminghaus, St. Louis, MO (US); Alison MacInnes, St. Louis, MO (US); Daniel R. Wright, St. Louis, MO (US); Junhua Zhang, St. Louis, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/653,772

(22) Filed: Jul. 19, 2017

(65) Prior Publication Data

US 2017/0311593 A1  Nov. 2, 2017

Related U.S. Application Data

(63) Continuation of application No. 14/440,789, filed as application No. PCT/US2013/068507 on Nov. 5, 2013, now Pat. No. 9,743,664.

(60) Provisional application No. 61/794,769, filed on Mar. 15, 2013, provisional application No. 61/722,700, filed on Nov. 5, 2012.

(51) Int. Cl.
| | |
|---|---|
| *A01N 37/02* | (2006.01) |
| *A01N 37/04* | (2006.01) |
| *A01N 37/40* | (2006.01) |
| *A01N 39/04* | (2006.01) |
| *A01N 57/20* | (2006.01) |
| *G09B 19/00* | (2006.01) |

(52) U.S. Cl.
CPC .............. *A01N 37/04* (2013.01); *A01N 37/02* (2013.01); *A01N 37/40* (2013.01); *A01N 39/04* (2013.01); *A01N 57/20* (2013.01); *G09B 19/00* (2013.01)

(58) Field of Classification Search
None
See application file for complete search history.

(56) References Cited

U.S. PATENT DOCUMENTS

| | | |
|---|---|---|
| 5,035,738 A | 7/1991 | Burns et al. |
| 5,389,598 A | 2/1995 | Berk et al. |
| 5,703,014 A | 12/1997 | Caulder et al. |
| 5,877,112 A | 3/1999 | Roberts et al. |
| 6,200,929 B1 | 3/2001 | Horibe et al. |
| 6,541,424 B2 | 4/2003 | Roberts et al. |
| 6,831,038 B2 | 12/2004 | Volgas et al. |
| 6,906,004 B2 | 6/2005 | Parrish et al. |
| 7,012,040 B2 | 3/2006 | Hacker et al. |
| 8,268,749 B2 | 9/2012 | Wright et al. |
| 8,337,900 B2 | 12/2012 | CasanGiner et al. |
| 8,987,167 B2 | 3/2015 | Xu et al. |
| 2002/0108415 A1 | 8/2002 | Volgas et al. |
| 2002/0160916 A1 | 10/2002 | Volgas et al. |
| 2006/0270557 A1 | 11/2006 | Volgas et al. |
| 2010/0248963 A1 | 9/2010 | Becher et al. |
| 2010/0331182 A1 | 12/2010 | Zhang et al. |
| 2011/0009269 A1 | 1/2011 | Gioia et al. |
| 2011/0034332 A1 | 2/2011 | Becher et al. |
| 2011/0166235 A1 | 7/2011 | Sun |
| 2012/0142532 A1 | 6/2012 | Wright et al. |
| 2012/0231956 A1 | 9/2012 | Rainbird |
| 2012/0238451 A1 | 9/2012 | Feng et al. |
| 2012/0289402 A1 | 11/2012 | Brown et al. |
| 2013/0079228 A1 | 3/2013 | Freed |
| 2013/0109572 A1 | 5/2013 | Pernak et al. |
| 2013/0109725 A1 | 5/2013 | Dave et al. |
| 2013/0225405 A1 | 8/2013 | Hixson et al. |
| 2014/0013654 A1 | 1/2014 | Burke |
| 2015/0057157 A1 | 2/2015 | Baseeth et al. |

FOREIGN PATENT DOCUMENTS

| | | |
|---|---|---|
| CN | 1176954 A | 3/1998 |
| CN | 101564044 A | 10/2009 |
| CN | 103371160 A | 10/2013 |
| WO | 9007275 | 7/1990 |
| WO | 1992012637 | 8/1992 |
| WO | 9410844 | 5/1994 |
| WO | 2000041567 | 7/2000 |
| WO | 0126463 | 4/2001 |
| WO | 2002011536 | 2/2002 |
| WO | 02069718 | 9/2002 |
| WO | 2004080177 | 9/2004 |
| WO | 2008077196 | 7/2008 |

(Continued)

OTHER PUBLICATIONS

AGRI STAR® Diacamba DMA Salt Label and Material Safety Data Sheet, Aug. 2012, Albaugh, Inc., Ankeny, Iowa, found at http://www.cdms.net/labelsmsds/LMDefault.aspx?pd=4887&t. (36 pages).
BANVEL® Herbicide Label and Material Safety Data Sheet, 1999, Arysta LifeScience North America, LLC, Cary, North Carolina, found at http://www.cdms.net/labelsmsds/LMDefault.aspx?pd=92 &t. (29 pages).
BARRAGE HF® Label, 2005, Helena Chemical Company, Collierville, Tennessee, Label found at http://www.helenachemical.com/specialty/Labels/Barrage%20HF%20(5905-529).pdf. (12 pages).
CLARITY® Herbicide Label, 2010, BASF Corporation, Research Triangle Park, North Carolina, found at http://www.cdms.net/LDat/Id797012.pdf. (22 pages).
DIABLO® Herbicide Label, 2011, Nufarm Americas Inc., Burr Ridge, Illinois, found at http://www.cdms.net/labelsmsds/LMDefault.aspx?pd=7398&t. (30 pages).

(Continued)

*Primary Examiner* — Alton N Pryor
(74) *Attorney, Agent, or Firm* — Stinson Leonard Street LLP; Erin C. Robert

(57) ABSTRACT

The present invention relates generally low volatility herbicidal compositions comprising at least one auxin herbicide and at least one monocarboxylic acid, or monocarboxylate thereof. The invention further relates generally to methods for preparing and using such low volatility herbicidal compositions, including methods for controlling auxin-susceptible plant growth on agricultural and non-agricultural lands.

45 Claims, No Drawings

(56) References Cited

FOREIGN PATENT DOCUMENTS

| WO | 2010053385 | 5/2010 |
|---|---|---|
| WO | 2013159731 | 10/2013 |

OTHER PUBLICATIONS

DISTINCT® Herbicide Label, Mar. 2012, BASF Corporation, Research Triangle Park, North Carolina, found at http://www.cdms.net/labelsmsds/LMDefault.aspx?pd=3700&t. (21 pages).
DURANGO® DMA® Herbicide Label, Jun. 2012, Dow AgroSciences LLC, Indianapolis, Indiana, found at http://www.cdms.net/labelsmsds/LMDefault.aspx?pd=8831&t_ (36 pages).
FORMULA 40® Herbicide Label with EPA Re-Registration Approval dated Sep. 16, 2008, Dow AgroSciences, LLC, Indianapolis, Indiana, Label found at http://www.cdms.net/labelsmsds/LMDefault.aspx?pd=8600&t, and EPA Letter found at http://iaspub.epa.gov/apex/pesticides/f?p=PPLS:102:::NO::P102_REG_NUM:62719-1. (45 pages).
HONCHO PLUS® Herbicide Label, 2010, Monsanto Company, St. Louis, Missouri, found at http://www.cdms.net/labelsmsds/LMDefault.aspx?pd=6296&t. (26 pages).
International Search Report and Written Opinion for International Application No. PCT/US2013/068507 dated May 12, 2014 (15 pages).
LIBERTY® 280 SL Herbicide Label, 2011, Bayer CropScience, Research Triangle Park, North Carolina, found at http://fs1.agrian.com/pdfs/Liberty_280_SL_Label2.pdf. (21 pages).
OPTI-AMINE® 2,4-D Amine Herbicide Label, Apr. 2012, Helena Chemical Company, Collierville, Tennessee, found at http://www.cdms.net/labelsmsds/LMDefault.aspx?pd=4410&t. (25 pages).
ORACLE® Dicamba Agricultural Herbicide Label, 2010, Gharda Chemicals Limited, Newtown, Pennsylvania, found at http://www.kellysolutions.com/ok/showproductinfo.asp?Product_Name=Oracle+Dicamba+Agricultural+Herbicide&EPA_Id=33658-30. (33 pages).
ROUNDUP POWERMAX® Herbicide Label, 2010, Monsanto Company, St. Louis, Missouri, found at http://www.cdms.net/labelsmsds/LMDefault.aspx?pd=8837&t. (54 pages).
ROUNDUP WEATHERMAX® Herbicide Label, 2007, Monsanto Company, St. Louis, Missouri, found at http://www.cdms.net/labelsmsds/LMDefault.aspx?pd=6026&t. (49 pages).
Strachan et al., "Vapor Movement of Synthetic Auxin Herbicides: Aminocyclopyrachlor, Aminocyclopyrachlor-Methyl Ester, Dicamba, and Aminopyralid" Weed Science, 58:103-108 (2010).
TOUCHDOWN PRO® Herbicide Label, 2010, Sygenta Crop Protection, Inc., Greensboro, North Carolina, found at http://www.cdms.net/labelsmsds/LMDefault.aspx?pd=4875&t. (29 pages).
TRAXION® Herbicide Label, 2011, Syngenta Crop Protection, Inc., Greensboro, North Carolina, found at http://www.syngentacropprotection.com/labels/default.aspx. (64 pages).
VANQUISH® Herbicide Label, 2011, Sygenta Crop Protection, Inc., Greensboro, North Carolina, found at http://tirmsdev.com/Syngenta-Professional-Products-Vanquish-Herbicide-p90. (8 pages).
VISION® Herbicide Label, Jul. 25, 2012, Helena Chemical Company, Collierville, Tennessee, found at http://www.cdms.net/LabelsMsds/LMDefault.aspx?pd=9280&t. (25 pages).
WEEDER 64® Broadleaf Herbicide Label with EPA Re-Registration Approval dated Sep. 8, 2010, Nufarms Americas Inc., Burr Ridge, Illinois, Label found at http://www.afpmb.org/sites/default/files/pubs/standardlists/labels/6840-00-577-4194_label.pdf, EPA Letter found at http://iaspub.epa.gov/apex/pesticides/f?p=PPLS:102:::NO:P102_REG_NUM:71368-1. (37 pages).

LOW VOLATILITY HERBICIDAL COMPOSITIONS

CROSS-REFERENCE TO RELATED APPLICATIONS

This is a continuation of U.S. application Ser. No. 14/440,789, filed May 5, 2015, which is a U.S. national stage application of International Patent Application No. PCT/US2013/068507, filed Nov. 5, 2013, which claims priority to U.S. Provisional Application Ser. No. 61/794,769 filed on Mar. 15, 2013 and U.S. Provisional Application Ser. No. 61/722,700 filed on Nov. 5, 2012, the entire disclosures of which are incorporated herein by reference.

FIELD OF THE INVENTION

The present invention relates generally to low volatility herbicidal compositions comprising at least one auxin herbicide and at least one monocarboxylic acid, or monocarboxylate thereof. The invention further relates generally to methods for preparing and using such low volatility herbicidal compositions, including methods for controlling auxin-susceptible plant growth on agricultural and non-agricultural lands.

BACKGROUND OF THE INVENTION

Auxin herbicides, such as dicamba (3,6-dichloro-2-methoxybenzoic acid) and 2,4-D (2,4-dichlorophenoxyacetic acid), are commonly used to control auxin-susceptible plant growth on both agricultural and non-agricultural lands. Volatility and drift, however, are problems frequently associated with these herbicides. Volatile auxin herbicides can, under certain application conditions, vaporize into the surrounding atmosphere and migrate from the application site to adjacent crop plants, such as soybeans and cotton, where contact damage to sensitive plants can occur. Spray drift can be attributed to both volatility and the physical movement of small particles from the target site to adjacent crop plants.

Prior approaches to reducing herbicide volatility have included efforts to identify herbicide salts and formulations exhibiting lower volatility. As one example, the diglycolamine salt of dicamba exhibits a lower volatility than the dimethylamine salt of dicamba. Although lower volatility auxin herbicide salts and formulations have been reported, further reduction in the volatility and off-target movement of auxin herbicides is still desirable.

Another approach to reducing auxin herbicide volatility has focused on encapsulation, for example, absorbing the auxin herbicide into solid phase natural or synthetic polymer, or microencapsulating the auxin herbicide in a polymer shell. Due to technological challenges and other factors, however, commercial encapsulation products that satisfactorily reduce auxin herbicide volatility have not been developed.

Accordingly, auxin herbicide compositions having reduced volatility relative to currently available compositions would be desirable, particularly reduced-volatility compositions that exhibit no significant reduction in herbicidal effectiveness relative to currently available compositions.

BRIEF DESCRIPTION OF THE INVENTION

In one aspect, the present invention provides herbicidal compositions comprising at least one auxin herbicide; at least one monocarboxylic acid, or agriculturally acceptable monocarboxylate thereof; and, optionally, a non-auxin herbicide; wherein the compositions exhibit reduced volatility relative to an otherwise identical composition lacking the monocarboxylic acid or monocarboxylate thereof. In one embodiment, the auxin herbicide is selected from dicamba, or a agriculturally acceptable salt or ester thereof, and 2,4-D, or an agriculturally acceptable salt of ester thereof. In one embodiment, the composition comprises an acetate salt. In another embodiment, the non-auxin herbicide is glyphosate, or an agriculturally acceptable salt thereof.

In another aspect, the invention provides a herbicidal adjuvant composition comprising a monocarboxylic acid, or monocarboxylate thereof, and, optionally, an alkali metal phosphate, that can serve as the source of monocarboxylic acid, or a monocarboxylate thereof, used in the preparation of the herbicidal compositions of the present invention.

In another aspect, the invention provides methods of reducing the volatility of an auxin herbicide, wherein the methods comprise the step of contacting an auxin herbicide with a volatility-lowering effective amount of a monocarboxylic acid, or a monocarboxylate thereof, thereby reducing the volatility of the auxin herbicide.

In another aspect, the invention provides methods of controlling the growth of auxin-susceptible plants, wherein the methods comprise applying to the auxin-susceptible plants a herbicidal composition application mixture comprising at least one auxin herbicide; at least one monocarboxylic acid, or monocarboxylate thereof; and, optionally, a non-auxin herbicide; wherein the application mixture exhibits reduced auxin herbicide volatility relative to an otherwise identical application mixture lacking the monocarboxylic acid, or monocarboxylate thereof.

In another aspect, the invention provides methods of controlling off-site movement of an auxin herbicide, wherein the methods comprise contacting the auxin herbicide with a volatility-lowering effective amount of a monocarboxylic acid, or a monocarboxylate thereof, prior to application of the auxin herbicide.

In another aspect, the invention provides methods of counseling an individual regarding the preparation and/or application of an auxin herbicide.

Further benefits of the present invention will be apparent to one skilled in the art from reading this patent application. The embodiments of the invention described in the following paragraphs are intended to illustrate the invention and should not be deemed to narrow the scope of the invention.

DETAILED DESCRIPTION OF THE INVENTION

The present invention provides herbicidal compositions comprising an auxin herbicide wherein the compositions exhibit reduced volatility and/or vapor drift upon application with respect to the auxin herbicide. Specifically, the compositions comprise, in addition to the auxin herbicide, at least one monocarboxylic acid, or monocarboxylate thereof, in an amount sufficient to reduce the volatility of the auxin herbicide relative to an otherwise identical composition lacking the monocarboxylic acid, or monocarboxylate thereof.

It has been discovered that the addition of a sufficient amount of a monocarboxylic acid, or a monocarboxylate thereof (particularly a non-ammoniated monocarboxylate salt), to a herbicidal composition concentrate (e.g., a "premix") or a herbicidal composition application mixture (e.g., a "tank mix") results in a significant reduction in the level of volatile auxin herbicide detected. For some compositions, the amount of volatile auxin herbicide present is actually below the detection level of sophisticated analytical methods such as liquid chromatography-mass spectrometry (LC/MS). As compared to auxin compositions known in the art, it is believed that the compositions of the present invention provide enhanced protection from off-target crop injury while maintaining comparable herbicidal efficacy on auxin-susceptible plants located in the target area.

The present invention is additionally directed to methods for controlling the growth of auxin-susceptible plants, comprising applying the herbicidal compositions of the present invention to such plants in accordance with the guidance provided below.

As used throughout this application, the term "agriculturally acceptable salt" refers to a salt comprising a cation that is known and accepted in the art for the formation of salts for agricultural or horticultural use. In one embodiment, the salt is a water-soluble salt.

A. AUXIN HERBICIDE COMPONENT

The term "auxin herbicide" refers to a herbicide that functions as a mimic of an auxin plant growth hormone, thereby affecting plant growth regulation. Examples of auxin herbicides that are suitable for use in the herbicidal compositions of the present invention include, without limitation, benzoic acid herbicides, phenoxy herbicides, pyridine carboxylic acid herbicides, pyridine oxy herbicides, pyrimidine carboxy herbicides, quinoline carboxylic acid herbicides, and benzothiazole herbicides.

Specific examples of auxin herbicides include:
Dicamba (3,6-dichloro-2-methoxy benzoic acid);
2,4-D (2,4-dichlorophenoxyacetic acid);
2,4-DB (4-(2,4-dichlorophenoxy)butanoic acid);
Dichloroprop (2-(2,4-dichlorophenoxy)propanoic acid);
MCPA ((4-chloro-2-methylphenoxy)acetic acid);
MCPB (4-(4-chloro-2-methylphenoxy)butanoic acid);
Aminopyralid (4-amino-3,6-dichloro-2-pyridinecarboxylic acid);
Clopyralid (3,6-dichloro-2-pyridinecarboxylic acid);
Fluoroxypyr ([(4-amino-3,5-dichloro-6-fluoro-2-pyridinyl)oxy]acetic acid);
Triclopyr ([(3,5,6-trichloro-2-pyridinyl)oxy]acetic acid);
Diclopyr;
Mecoprop (2-(4-chloro-2-methylphenoxy)propanoic acid);
Mecoprop-P;
Picloram (4-am ino-3,5,6-trichloro-2-pyridinecarboxylic acid);
Quinclorac (3,7-dichloro-8-quinolinecarboxylic acid); and
Aminocyclopyrachlor (6-am ino-5-chloro-2-cyclopropyl-4-pyrimidinecarboxylic acid);
including salts and esters thereof; racemic mixtures and resolved isomers thereof; and combinations thereof.

In one embodiment, the herbicidal composition comprises dicamba, or an agriculturally acceptable salt or ester thereof. Examples of suitable dicamba salts include the N,N-bis-[aminopropyl]methylamine, monoethanolamine, dimethylamine (e.g., BANVEL®, ORACLE®, etc.), isopropylamine, diglycolamine (e.g., CLARITY®, VANQUISH®, etc.), potassium, and sodium salts, and combinations thereof. Commercially available sources of dicamba, and its agriculturally acceptable salts, include those products sold under the trade names BANVEL®, CLARITY®, DIABLO®, DISTINCT, ORACLE®, VANQUISH®, and VISION®.

In another embodiment, the herbicidal composition comprises an agriculturally acceptable dicamba salt, wherein the salt is selected from the group consisting of N,N-bis-[aminopropyl]methylamine, monoethanolamine, dimethylamine, isopropylamine, diglycolamine, potassium, and sodium salts, and combinations thereof.

Throughout the remainder of the description of the invention, where reference is made to dicamba, or an agriculturally acceptable salt or ester thereof, one skilled in the art will understand that the principles of the present invention apply to auxin herbicides generally, including those described above, and that the present invention is not limited to herbicidal compositions containing dicamba, or an agriculturally acceptable salt or ester thereof.

In another embodiment, the herbicidal composition comprises 2,4-D, or an agriculturally acceptable salt or ester thereof. Examples of suitable 2,4-D salts include the choline, dimethylamine, and isopropylamine salts, and combinations thereof. Examples of suitable 2,4-D esters include the methyl, ethyl, propyl, butyl (2,4-DB), and isooctyl esters, and combinations thereof. Commercially available sources of 2,4-D, and its agriculturally acceptable salts and esters, include those products sold under the trade names BARRAGE®, FORMULA 40®, OPT-AMINE®, and WEEDAR 64®.

In another embodiment, the herbicidal composition comprises an agriculturally acceptable 2,4-D salt, wherein the salt is selected from the group consisting of choline, dimethylamine, and isopropylamine salts, and combinations thereof.

In another embodiment, the herbicidal composition comprises an agriculturally acceptable 2,4-D ester, wherein the ester is selected from the group consisting of butyl (i.e., 2,4-DB) and isooctyl esters, and combinations thereof.

In another embodiment, the herbicidal composition comprises at least two auxin herbicides, for example, dicamba, or an agriculturally acceptable salt or ester thereof, and 2,4-D, or an agriculturally acceptable salt or ester thereof.

In another embodiment, the herbicidal composition comprises an agriculturally acceptable auxin herbicide salt (such as a dicamba salt, a 2,4-D salt, and/or a 2,4-DB salt) that is an ionic liquid as described in published application US2013/0109572, i.e., a salt that is a liquid at a temperature at or below about 150° C. The entire text of US2013/0109572 is incorporated by reference into this application.

B. MONOCARBOXYLIC ACID/MONOCARBOXYLATE COMPONENT

"Monocarboxylic acid" refers to a hydrocarbon or substituted hydrocarbon containing only one carboxy functional group (i.e., $R^1$—C(O)OH). "Monocarboxylate" refers to a salt (i.e., $R^1$—C(O)OM wherein M is an agriculturally acceptable cation) or ester (i.e., $R^1$—C(O)OR$^2$ wherein $R^2$ is hydrocarbon or substituted hydrocarbon) of a monocarboxylic acid. In one embodiment, the composition comprises at least one monocarboxylate salt, which in aqueous compositions may be present, in whole or in part, in dissociated form as a monocarboxylate anion and the corresponding cation.

Representative monocarboxylic acids and monocarboxylates generally comprise a hydrocarbon or unsubstituted hydrocarbon selected from, for example, unsubstituted or substituted, straight or branched chain alkyl (e.g., $C_1$-$C_{20}$ alkyl such as methyl, ethyl, n-propyl, isopropyl, etc.); unsubstituted or substituted, straight or branched chain alkenyl (e.g., $C_2$-$C_{20}$ alkyl such as ethenyl, n-propenyl, isopropenyl, etc.); unsubstituted or substituted aryl (e.g., phenyl, hydroxyphenyl, etc.); or unsubstituted or substituted arylalkyl (e.g., benzyl). In one embodiment, the monocarboxylic acid is selected from the group consisting of formic acid, acetic acid, propionic acid, and benzoic acid. In another embodiment, the monocarboxylate salt is selected from the group consisting of formate salts, acetate salts, propionate salts, and benzoate salts.

In one embodiment, the herbicidal composition comprises a monocarboxylate salt having the formula $R^1$—C(O)OM, wherein $R^1$ is unsubstituted or substituted $C_1$-$C_{10}$ alkyl and M is a non-ammoniated, agriculturally acceptable cation. In another embodiment, the herbicidal composition comprises a monocarboxylate salt having the formula $R^1$—C(O)OM, wherein $R^1$ is unsubstituted $C_1$-$C_6$ alkyl and M is an alkali metal salt. In another embodiment, the herbicidal composition comprises a monocarboxylate salt having the formula $R^1$—C(O)OM, wherein $R^1$ is unsubstituted $C_1$-$C_3$ alkyl and M is an alkali metal salt selected from sodium and potassium. In another embodiment, the monocarboxylate salt is potassium acetate. In another embodiment, the monocarboxylate salt is sodium acetate.

C. ALKALI METAL PHOSPHATE/ALKALI METAL CARBONATE

The herbicidal compositions of the present invention optionally may further comprise an alkali metal phosphate such as dipotassium phosphate. Dipotassium phosphate, for example, can provide additional buffering and/or water-conditioning for aqueous herbicidal compositions of the present invention. Dipotassium phosphate is particularly effective as a replacement for ammonium sulfate in herbicidal composition application mixtures prepared using hard water.

Similarly, the herbicidal compositions of the present invention optionally may further comprise an alkali metal carbonate, such as potassium carbonate, to provide additional buffering and/or water-conditioning for aqueous herbicidal compositions of the present invention.

In some embodiments, the herbicidal compositions of the present invention comprise an alkali metal phosphate. In other embodiments, the herbicidal compositions comprise an alkali metal carbonate. In still other embodiments, the herbicidal compositions comprise an alkali metal phosphate and an alkali metal carbonate.

D. NON-HERBICIDE ADDITIVES

The herbicidal compositions of the present invention optionally may further comprise conventional additives such as surfactants, drift reduction agents, safeners, solubility enhancing agents, thickening agents, flow enhancers, foam-moderating agents, freeze protectants, UV protectants, preservatives, antimicrobials, and/or other additives that are necessary or desirable to improve the performance, crop safety, or handling of the composition.

In one embodiment, the herbicidal composition comprises less than about 10 ppm of ammonium sulfate. In another embodiment, the herbicidal composition does not comprise ammonium sulfate.

In one embodiment, the herbicidal composition does not comprise an acid other than a monocarboxylic acid.

E. NON-AUXIN HERBICIDE COMPONENTS

The herbicidal compositions of the present invention optionally may further comprise at least one non-auxin herbicide. The term "non-auxin herbicide" refers to a herbicide having a primary mode of action other than as an auxin herbicide. Representative examples of non-auxin herbicides include acetyl CoA carboxylase (ACCase) inhibitors, acetolactate synthase (ALS) inhibitors, acetohydroxy acid synthase (AHAS) inhibitors, photosystem II inhibitors, photosystem I inhibitors, protoporphyrinogen oxidase (PPO or Protox) inhibitors, carotenoid biosynthesis inhibitors, enolpyruvyl shikimate-3-phosphate (EPSP) synthase inhibitor, glutamine synthetase inhibitor, dihydropteroate synthetase inhibitor, mitosis inhibitors, and nucleic acid inhibitors; salts and esters thereof; racemic mixtures and resolved isomers thereof; and combinations thereof.

Representative examples of ACCase inhibitors include clethodim, clodinafop, fenoxaprop-P, fluazifop-P, quizalofop-P, and sethoxydim.

Representative examples of ALS or AHAS inhibitors include flumetsulam, imazamethabenz-m, imazamox, imazapic, imazapyr, imazaquin, imazethapyr, metsulfuron, prosulfuron, and sulfosulfuron.

Representative examples of photosystem I inhibitors include diquat and paraquat.

Representative examples of photosystem II inhibitors include atrazine, cyanazine, diuron, and metibuzin.

Representative examples of PPO inhibitors include acifluorofen, butafenacil, carfentrazone-ethyl, flufenpyr-ethyl, fluthiacet, flumiclorac, flumioxazin, fomesafen, lactofen, oxadiazon, oxyfluorofen, and sulfentrazone.

Representative examples of carotenoid biosynthesis inhibitors include aclonifen, amitrole, diflufenican, mesotrione, and sulcotrione.

A representative example of an EPSP inhibitor is N-phosphonomethyl glycine (glyphosate).

A representative example of a glutamine synthetase inhibitor is glufosinate.

A representative example of a dihydropteroate synthetase inhibitor is asulam.

Representative examples of mitosis inhibitors include acetochlor, alachlor, dithiopyr, S-metolachlor, and thiazopyr.

Representative examples of nucleic acid inhibitors include difenzoquat, fosamine, metham, and pelargonic acid.

In one embodiment, the herbicidal compositions of the present invention further comprise a non-auxin herbicide selected from the group consisting of acetochlor, glyphosate, glufosinate, flumioxazin, fomesafen, and agriculturally acceptable salts thereof.

In one embodiment, the herbicidal compositions of the present invention further comprise glyphosate, or an agriculturally acceptable salt thereof. Suitable glyphosate salts include, for example, the ammonium, diammonium, dimethylammonium, monoethanolamine, isopropylamine, and potassium salts, and combinations thereof. In one embodiment, the glyphosate salts are selected from the group consisting of monoethanolamine, isopropylamine, and potassium salts, and combinations thereof.

In one embodiment, the herbicidal compositions of the present invention further comprise glufosinate, or an agriculturally acceptable salt thereof.

In one embodiment, the herbicidal compositions of the present invention comprise dicamba, or an agriculturally acceptable salt or ester thereof, and glyphosate, or an agriculturally acceptable salt thereof. In another embodiment, the herbicidal compositions of the present invention comprise dicamba, or an agriculturally acceptable salt thereof; glyphosate, or an agriculturally acceptable salt thereof; and a non-ammoniated, agriculturally acceptable acetate salt. Commercially available sources of glyphosate, and its agriculturally acceptable salts, include those products sold under the trade names DURANGO® DMA®, HONCHO PLUS®, ROUNDUP POWERMAX®, ROUNDUP WEATHERMAX®, TRAXION®, and TOUCHDOWN®.

In one embodiment, the herbicidal compositions of the present invention comprise 2,4-D, or an agriculturally acceptable salt or ester thereof, and glyphosate, or an agriculturally acceptable salt thereof. In another embodiment, the herbicidal compositions of the present invention comprise 2,4-D, or an agriculturally acceptable salt or ester thereof; glyphosate, or an agriculturally acceptable salt thereof; and a non-ammoniated, agriculturally acceptable acetate salt.

In another embodiment, the herbicidal composition comprises an agriculturally acceptable non-auxin herbicide salt (such as a glyphosate salt) that is an ionic liquid as described in published application US2013/0109572, i.e., a salt that is a liquid at a temperature at or below about 150° C.

F. COMPONENT LOADING

Suitable amounts, concentrations, and/or molar ratios of the auxin herbicide, monocarboxylic acid, or monocarboxylate thereof, and optional non-auxin herbicide and non-herbicide additive components of the herbicidal compositions of the present invention will depend to some extent upon whether the composition is a ready-to-use composition, a concentrate to be diluted with water prior to application (e.g., a "premix"), or a herbicidal composition prepared by combining two or more herbicide components, water, and, optionally, other non-herbicide components (e.g., a "tank mix").

1. Herbicide Loading:

Concentrated herbicidal compositions of the present invention typically comprise on an acid equivalent basis (a.e.), for example, from about 120 to about 600 g a.e./L, from about 300 to about 600 g a.e./L, from about 350 to about 600 g a.e./L, from about 400 to about 600 g a.e./L, from about 450 to about 600 g a.e./L, or from about 500 to about 600 g a.e./L total herbicide loading. Additional examples of representative total herbicide loading include about 120, 150, 200, 250, 300, 350, 400, 450, 500, 550, and 600 g a.e./L, and ranges thereof (i.e., from about 120 to about 150 g a.e./L, from about 150 to about 200 g a.e./L, from about 200 to about 250 g a.e./L, from about 250 to about 300 g a.e./L, from about 300 to about 350 g a.e./L, from about 350 to about 400 g a.e./L from about 400 to about 450 g a.e./L, from about 450 to about 500 g a.e./L, from about 500 to about 550 g a.e./L, from about 550 to about 600 g a.e./L total herbicide loading).

In certain embodiments, the herbicidal composition is a liquid concentrate containing, for example, a total amount (acid equivalent weight) of herbicide from about 5% to about 75% by weight of the concentrate. In one aspect, the amount is from about 10% to about 60% by weight of the concentrate. In another aspect, the amount is from about 15% to about 50% by weight of the concentrate. In another aspect, the amount is from about 20% to about 40% by weight of the concentrate. In another aspect, the amount is from about 25% to about 35% by weight of the concentrate. In another aspect, the amount is about 30% by weight of the concentrate.

In certain embodiments, the herbicidal composition is a dry concentrate (e.g., powder or granules) containing, for example, a total amount (acid equivalent weight) of herbicide from about 40% to about 90% by weight of the concentrate. In one aspect, the amount is from about 50% to about 80% by weight of the concentrate. In another aspect, the amount is from about 60% to about 75% by weight of the concentrate. In another aspect, the amount is from about 65% to about 70% by weight of the concentrate.

Ready-to-use herbicidal compositions and other herbicidal compositions of the present invention requiring no further processing prior to application (e.g., diluted concentrates, tank mixes, etc.) typically will comprise on an acid equivalent basis (a.e.) from about 0.1 g a.e./L to about 50 g a.e./L total herbicide loading. Additional examples of representative total herbicide loading for such compositions include about 0.5, 1, 2, 3, 4, 5, 6, 7, 8, 9, 10, 15, 20, 25, 30, 35, 40, 45, and 50 g a.e./L, and ranges thereof (e.g., from about 0.5 to about 5 g a.e./L, from about 5 to about 10 g a.e./L, from about 10 to about 15 g a.e./L, from about 15 to about 20 g a.e./L, from about 20 to about 25 g a.e./L, from about 25 to about 30 g a.e./L from about 30 to about 35 g a.e./L, from about 35 to about 40 g a.e./L, from about 40 to about 45 g a.e./L, from about 45 to about 50 g a.e./L total herbicide loading).

In herbicidal compositions of the present invention comprising an auxin herbicide and a non-auxin herbicide, the weight ratio on an acid equivalent basis of the auxin herbicide to the non-auxin herbicide is typically no greater than about 50:1, for example, about 50:1, 25:1, 10:1, 5:1, 3:1, 2:1, 1:1, 1:2, 1:3, 1:5, about 1:10, or ranges thereof such as from about 50:1 to about 1:10, from about 50:1 to about 1:5, from about 50:1 to about 1:1, from about 50:1 to about 3:1, from about 50:1 to about 5:1, from about 50:1 to about 10:1, from about 25:1 to about 1:1, or from about 25:1 to about 3:1.

For any given auxin herbicide, one skilled in the art can readily determine using routine experimentation a minimum concentration of auxin herbicide and a minimum ratio of auxin herbicide to any additional auxin herbicides and/or non-auxin herbicides contained in the herbicidal composition that is desirable for the intended application.

2. Monocarboxylic Acid/Monocarboxylate Loading:

As previously noted, it has been discovered that the concentration of volatilized auxin herbicide in the vapor phase surrounding a herbicidal composition comprising an auxin herbicide and a monocarboxylic acid, or monocarboxylate thereof, is less than the concentration of volatilized auxin herbicide in the vapor phase surrounding a reference composition lacking the monocarboxylic acid or monocarboxylate, but otherwise having the same composition. In various embodiments, the concentration of volatilized auxin herbicide in the vapor phase surrounding a herbicidal composition comprising an auxin herbicide and a monocarboxylic acid, or monocarboxylate thereof, is less than about 90%, 80%, 70%, 60%, 50%, 40%, 30%, 20%, 10%, or 5% Δ of the concentration of volatilized auxin herbicide in the vapor phase surrounding the reference composition lacking the monocarboxylate.

The herbicidal compositions of the present invention may comprise a single monocarboxylic acid, or monocarboxylate thereof, or a mixture of two or more monocarboxylic acids, or monocarboxylates thereof.

The monocarboxylic acid or monocarboxylate loading of the herbicidal composition generally will depend upon the auxin herbicide loading of the herbicidal composition, the salt form of the auxin herbicide, and the properties of any other components of the herbicidal composition, and will be an amount sufficient to reduce the volatility of the auxin herbicide relative to a reference composition lacking the monocarboxylic acid or monocarboxylate, but otherwise having the same composition. For example, the monoethanolamine and diethanolamine salts of dicamba are less volatile than the dimethylamine and isopropylamine salts of dicamba and the loading required for the less volatile salts may be less than the loading required for the more volatile salts. In addition, the loading of the monocarboxylic acid, or monocarboxylate thereof, can vary with the specific combination of auxin herbicide, optional non-auxin herbicide, and monocarboxylic acid, or monocarboxylate thereof.

In the herbicidal compositions of the present invention the molar ratio of the auxin herbicide to the monocarboxylic acid, or monocarboxylate thereof, is typically no less than about 1:10 and no greater than about 10:1. Representative molar ratios of auxin herbicide acid equivalent (a.e.) to total monocarboxylic acid, or monocarboxylate thereof, are, for example, from 1:10 to about 10:1, from about 1:5 to about 5:1, and from about 3:1 to about 1:3. In one aspect, the molar ratio of auxin herbicide to monocarboxylic acid, or monocarboxylate thereof, is about 2:1 to about 1:2. In another aspect, the molar ratio of auxin herbicide to monocarboxylic acid, or monocarboxylate thereof, is about 1:1.

In certain embodiments, the herbicidal composition concentrates of the present invention contain an amount (acid equivalent weight) of the monocarboxylic acid, or monocarboxylate thereof, from about 0.25% to about 25% by weight of the concentrate. In one aspect, the amount is from about 1% to about 20% by weight of the concentrate. In another aspect, the amount is from about 2% to about 15% by weight of the concentrate. In another aspect, the concentrate is a liquid concentrate and the amount (acid equivalent weight) is from about 2% to about 10% by weight of the concentrate. In another aspect, the concentrate is a dry concentrate and the amount (acid equivalent weight) is from about 5% to about 15% by weight of the concentrate. In another aspect, the monocarboxylic acid, or monocarboxylate thereof, is acetic acid, or agriculturally acceptable salt thereof.

In certain embodiments, the herbicidal composition tank mixes of the present invention contain an amount (acid equivalent weight) of the monocarboxylic acid, or monocarboxylate thereof, from about 0.01% to about 25% by weight of the tank mix. In one aspect, the amount is from about 0.01% to about 20% by weight of the tank mix. In another aspect, the amount is from about 0.05% to about 15% by weight of the tank mix. In another aspect, the amount is from about 0.05% to about 10% by weight of the tank mix. In another aspect, the amount is from about 0.05% to about 5% by weight of the tank mix. In another aspect, the amount is from about 0.1% to about 2% by weight of the tank mix. In another aspect, the amount is from about 0.1% to about 1% by weight of the tank mix. In another aspect, the monocarboxylic acid, or monocarboxylate thereof, is acetic acid, or agriculturally acceptable salt thereof.

3. Alkali Metal Phosphate/Alkali Metal Carbonate Loading

When the herbicidal composition comprises an alkali metal phosphate, such as dipotassium phosphate, the molar ratio of the alkali metal phosphate to the monocarboxylic acid, or monocarboxylate thereof, can range, for example, from about 1:5 to about 5:1, from about 3:1 to about 1:3, or from about 2:1 to about 1:2. In one embodiment, the molar ratio of alkali metal phosphate to monocarboxylic acid, or monocarboxylate thereof, is about 1:1.

When the herbicidal composition comprises an alkali metal carbonate, such as potassium carbonate, the molar ratio of the alkali metal carbonate to the monocarboxylic acid, or monocarboxylate thereof, can range, for example, from about 1:5 to about 5:1, from about 3:1 to about 1:3, or from about 2:1 to about 1:2. In one embodiment, the molar ratio of alkali metal carbonate to monocarboxylic acid, or monocarboxylate thereof, is about 1:1.

G. HERBICIDAL COMPOSITION EMBODIMENTS

The herbicidal compositions can be presented in various forms depending upon the intended use and handling properties desired. For example, the herbicidal compositions of the present invention can be prepared in dry form (e.g., powders, granules, etc.) or in liquid form (e.g., aqueous solutions, dispersions, etc.). The term "aqueous" as used in this application, however, is not intended to exclude the presence of non-aqueous (i.e., organic) solvents as long as water is present. Water is the predominant component of the ready-to-use compositions and tank mix compositions disclosed in this application.

Among the various composition presentations of the invention are the following:

(a) a ready-to-use aqueous herbicidal composition that can be applied to unwanted plants without the need for further dilution with water or other preparation;

(b) a herbicidal composition concentrate that is diluted with water, and optionally combined with other herbicide and non-herbicide materials, prior to application (including, e.g., dry mixes and premixes);

(c) a herbicidal composition application mixture prepared by diluting a herbicidal composition concentrate with water to form the herbicidal composition application mixture which then can be applied to auxin-susceptible plants;

(d) a herbicidal composition application mixture prepared by combining two or more separate components with water (e.g., a tank mix) to form the herbicidal composition application mixture which then can be applied to auxin-susceptible plants; and (e) a herbicidal composition application mixture prepared by introducing separate feed streams to a spraying or application system so that the feed streams are co-mixed to form the herbicidal composition application mixture immediately prior to use.

In various embodiments, the herbicidal compositions (ready-to-use, liquid concentrate, tank mix, etc.) have a pH that is equal to or higher than the acid dissociation constant (pKa) of the monocarboxylic acid present in the composition. For example, in certain embodiments, the herbicidal compositions comprise acetic acid (which has a pKa of about 4.8) and have a pH equal to or greater than about 4.8. In the case of herbicidal compositions comprising dicamba and an effective amount of acetic acid, dicamba volatility generally decreases as composition pH increases with dicamba volatility reaching substantially non-detectable levels at a composition pH of about 5.2 as measured in a plant response study.

1. Illustrative Composition Embodiments (Auxin Herbicide Concentrates)

One embodiment of the invention is directed to a herbicidal composition concentrate comprising:

at least one auxin herbicide; and at least one monocarboxylic acid, or a monocarboxylate thereof;

wherein the concentrate satisfies one or more of the following conditions:

the molar ratio of monocarboxylic acid, or monocarboxylate thereof, to auxin herbicide is from about 1:10 to about 10:1;

the acid equivalent weight ratio of monocarboxylic acid, or monocarboxylate thereof, to auxin herbicide is from about 1:10 to about 5:1;

the concentrate contains an amount (acid equivalent weight) of the monocarboxylic acid, or monocarboxylate thereof, from about 0.25% to about 25% by weight of the concentrate;

the concentration of the monocarboxylic acid, or monocarboxylate thereof, is from about 1 gram (acid equivalent weight)/L to about 250 grams (acid equivalent weight)/L; and the concentrate comprises an amount of the monocarboxylic acid, or monocarboxylate thereof, sufficient to reduce the concentration of volatilized auxin herbicide in the vapor phase surrounding the concentrate by at least about 10% relative to the concentration of volatilized auxin herbicide in the vapor phase surrounding an otherwise identical concentrate lacking the monocarboxylic acid, or monocarboxylate thereof.

In further embodiments, the herbicidal composition concentrate comprises at least one auxin herbicide selected from the group consisting of dicamba, or an agriculturally acceptable salt or ester thereof, and 2,4-D, or an agriculturally acceptable salt or ester thereof.

In further embodiments, the herbicidal composition concentrate comprises dicamba, or an agriculturally acceptable salt or ester thereof. In another embodiment, the concentrate comprises a dicamba salt selected from the group consisting of N,N-bis-[aminopropyl]methylamine, monoethanolamine, dimethylamine, isopropylamine, diglycolamine, potassium, and sodium salts, and combinations thereof.

In further embodiments, the herbicidal composition concentrate comprises 2,4-D, or an agriculturally acceptable salt or ester thereof. In another embodiment, the concentrate comprises a 2,4-D salt selected from the group consisting of choline, dimethylamine, and isopropylamine salts, and combinations thereof. In another embodiment, the concentrate comprises a 2,4-D ester selected from the group consisting of butyl (i.e., 2,4-DB) and isooctyl esters, and combinations thereof.

In further embodiments, the herbicidal composition concentrate comprises a monocarboxylate salt.

In further embodiments, the herbicidal composition concentrate comprises a $C_1$-$C_6$-alkanoic acid, or an agriculturally acceptable salt thereof. In other embodiments, the herbicidal composition concentrate comprises a $C_1$-$C_5$-alkanoic acid, or an agriculturally acceptable salt thereof. In other embodiments, the herbicidal composition concentrate comprises a $C_1$-$C_4$-alkanoic acid, or an agriculturally acceptable salt thereof. In other embodiments, the herbicidal composition concentrate comprises a $C_1$-$C_3$-alkanoic acid, or an agriculturally acceptable salt thereof. In other embodiments, the herbicidal composition concentrate comprises acetic acid, or an agriculturally acceptable salt thereof. In other embodiments, the herbicidal composition concentrate comprises formic acid, or an agriculturally acceptable salt thereof.

In further embodiments, the monocarboxylate salt or acetate salt is a non-ammoniated salt. In another embodiment, the monocarboxylate salt or acetate salt is an alkali metal salt. In another embodiment, the monocarboxylate salt or acetate salt is a potassium salt. In another embodiment, the monocarboxylate salt or acetate salt is a sodium salt.

In further embodiments, the herbicidal composition concentrate further comprises a buffer.

In further embodiments, the herbicidal composition concentrate further comprises an alkali metal phosphate, such as dipotassium phosphate.

In further embodiments, the herbicidal composition concentrate is a dry powder herbicidal composition.

In further embodiments, the herbicidal composition concentrate is an aqueous herbicidal composition.

In further embodiments, the herbicidal composition concentrate further comprises a non-auxin herbicide. In another embodiment, the non-auxin herbicide is selected from the group consisting of acetochlor, glyphosate, glufosinate, flumioxazin, fomesafen, and agriculturally acceptable salts thereof. In another embodiment, the non-auxin herbicide is glyphosate, or an agriculturally acceptable salt thereof. In another embodiment, the concentrate comprises a glyphosate salt selected from the group consisting of ammonium, diammonium, dimethylammonium, monoethanolamine, isopropylamine, and potassium salts, and combinations thereof. In another embodiment, the concentrate comprising a non-auxin herbicide satisfies one or more of the following conditions:

the sum of the concentration of auxin herbicide and the concentration of non-auxin herbicide is from about 120 grams (acid equivalent weight)/L to about 600 grams (acid equivalent weight)/L;

the acid equivalent weight ratio of auxin herbicide to non-auxin herbicide herbicide is from about 1:5 to about 2:1; and the acid equivalent weight ratio of monocarboxylic acid, or monocarboxylate thereof, to auxin herbicide is from about 1:10 to about 5:1.

In further embodiments, the herbicidal composition concentrate has a pH greater than or equal to the $pK_a$ of the monocarboxylic acid selected for the composition.

2. Illustrative Composition Embodiments (Auxin Herbicide Application Mixtures)

One embodiment of the invention is directed to a herbicidal composition comprising:

at least one auxin herbicide; and at least one monocarboxylic acid, or a monocarboxylate thereof;

wherein the composition satisfies one or more of the following conditions:

the molar ratio of monocarboxylic acid, or monocarboxylate thereof, to auxin herbicide is from about 1:10 to about 10:1;

the acid equivalent weight ratio of monocarboxylic acid, or monocarboxylate thereof, to auxin herbicide is from about 1:10 to about 5:1;

the composition contains an amount (acid equivalent weight) of the monocarboxylic acid, or monocarboxylate thereof, from about 0.01% to about 25 by weight of the composition;

the concentration of the monocarboxylic acid, or monocarboxylate thereof, is from about 1 gram (acid equivalent weight)/L to about 250 grams (acid equivalent weight)/L; and the composition comprises an amount of the monocarboxylic acid, or monocarboxylate thereof, sufficient to reduce the concentration of volatilized auxin herbicide in the vapor phase surrounding the composition by at least about 10% relative to the concentration of volatilized auxin herbicide in the vapor phase surrounding an otherwise identical composition lacking the monocarboxylic acid, or monocarboxylate thereof.

In one aspect, the composition contains an amount (acid equivalent weight) of the monocarboxylic acid, or monocarboxylate thereof, from about 0.1% to about 25% by weight of the composition.

In further embodiments, the composition comprises at least one auxin herbicide selected from the group consisting of dicamba, or an agriculturally acceptable salt or ester thereof, and 2,4-D, or an agriculturally acceptable salt or ester thereof.

In further embodiments, the composition comprises dicamba, or an agriculturally acceptable salt or ester thereof. In another embodiment, the composition comprises a dicamba salt selected from the group consisting of N,N-bis [aminopropyl]methylamine, monoethanolamine, dimethylamine, isopropylamine, diglycolamine, potassium, and sodium salts, and combinations thereof.

In further embodiments, the composition comprises 2,4-D, or an agriculturally acceptable salt or ester thereof. In another embodiment, the composition comprises a 2,4-D salt selected from the group consisting of choline, dimethylamine, and isopropylamine salts, and combinations thereof. In another embodiment, the composition comprises a 2,4-D ester such as 2,4-DB.

In further embodiments, the composition comprises a monocarboxylate salt.

In further embodiments, the herbicidal composition concentrate comprises a $C_1$-$C_6$-alkanoic acid, or an agriculturally acceptable salt thereof. In other embodiments, the herbicidal composition concentrate comprises a $C_1$-$C_5$-alkanoic acid, or an agriculturally acceptable salt thereof. In other embodiments, the herbicidal composition concentrate comprises a $C_1$-$C_4$-alkanoic acid, or an agriculturally acceptable salt thereof. In other embodiments, the herbicidal composition concentrate comprises a $C_1$-$C_3$-alkanoic acid, or an agriculturally acceptable salt thereof. In other embodiments, the herbicidal composition concentrate comprises acetic acid, or an agriculturally acceptable salt thereof. In other embodiments, the herbicidal composition concentrate comprises formic acid, or an agriculturally acceptable salt thereof.

In further embodiments, the monocarboxylate salt or acetate salt is a non-ammoniated salt. In another embodiment, the monocarboxylate salt or acetate salt is an alkali metal salt. In another embodiment, the monocarboxylate salt or acetate salt is a potassium salt. In another embodiment, the monocarboxylate salt or acetate salt is a sodium salt.

In further embodiments, the composition further comprises a buffer.

In further embodiments, the herbicidal composition concentrate further comprises an alkali metal phosphate, such as dipotassium phosphate.

In further embodiments, the composition is an aqueous herbicidal composition.

In further embodiments, the composition further comprises a non-auxin herbicide. In another embodiment, the non-auxin herbicide is selected from the group consisting of acetochlor, glyphosate, glufosinate, flumioxazin, fomesafen, and agriculturally acceptable salts thereof. In another embodiment, the non-auxin herbicide is glyphosate, or an agriculturally acceptable salt thereof. In another embodiment, the concentrate comprises a glyphosate salt selected from the group consisting of ammonium, diammonium, dimethylammonium, monoethanolamine, isopropylamine, and potassium salts, and combinations thereof. In another embodiment, the concentrate comprising a non-auxin herbicide satisfies one or more of the following conditions:

the sum of the concentration of auxin herbicide and the concentration of non-auxin herbicide is from about 1 gram (acid equivalent weight)/L to about 50 grams (acid equivalent weight)/L;

the acid equivalent weight ratio of auxin herbicide to non-auxin herbicide is from about 1:5 to about 2:1; and the acid equivalent weight ratio of monocarboxylic acid, or monocarboxylate thereof, to auxin herbicide is from about 1:10 to about 5:1.

3. Illustrative Composition Embodiments (Dicamba Concentrate)

Compositions of particular interest include herbicidal compositions comprising dicamba, or an agriculturally acceptable salt or ester thereof; acetic acid, or an agriculturally acceptable salt thereof; and, optionally, glyphosate, or an agriculturally acceptable salt thereof.

One embodiment of the invention is directed to a herbicidal composition concentrate comprising:

dicamba, or an agriculturally acceptable salt or ester thereof; and acetic acid, or an agriculturally acceptable salt thereof;

wherein the molar ratio of acetic acid, or agriculturally acceptable salt thereof, to dicamba, or agriculturally acceptable salt or ester thereof, is from about 1:10 to about 10:1.

In another embodiment, the herbicidal composition concentrate comprises:

(a) dicamba, or an agriculturally acceptable salt or ester thereof; and (b) acetic acid, or an agriculturally acceptable salt thereof;

wherein the acid equivalent weight ratio of acetic acid, or agriculturally acceptable salt thereof, to dicamba, or agriculturally acceptable salt or ester thereof, is from about 1:10 to about 5:1.

In another embodiment, the herbicidal composition concentrate comprises:

(a) dicamba, or an agriculturally acceptable salt or ester thereof; and (b) acetic acid, or an agriculturally acceptable salt thereof;

wherein the concentrate contains an amount (acid equivalent weight) of the acetic acid, or agriculturally acceptable salt thereof, from about 0.25% to about 25% by weight of the concentrate.

In another embodiment, the herbicidal composition concentrate comprises:

(a) dicamba, or an agriculturally acceptable salt or ester thereof; and (b) acetic acid, or an agriculturally acceptable salt thereof;

wherein the concentration of the acetic acid, or agriculturally acceptable salt thereof, is from about 1 gram (acid equivalent weight)/L to about 250 grams (acid equivalent weight)/L.

In another embodiment, the herbicidal composition concentrate comprises:

(a) dicamba, or an agriculturally acceptable salt or ester thereof; and (b) acetic acid, or an agriculturally acceptable salt thereof;

wherein the concentration of dicamba, or an agriculturally acceptable salt or ester thereof, is from about 120 grams (acid equivalent weight)/L to about 600 grams (acid equivalent weight)/L.

In another embodiment, the herbicidal composition concentrate comprises:

(a) dicamba, or an agriculturally acceptable salt or ester thereof; and (b) acetic acid, or an agriculturally acceptable salt thereof;

wherein the concentration of dicamba, or an agriculturally acceptable salt or ester thereof, is from about 120 grams (acid equivalent weight)/L to about 600 grams (acid equivalent weight)/L; and wherein the acid equivalent weight ratio of acetic acid, or agriculturally acceptable salt thereof, to dicamba, or agriculturally acceptable salt or ester thereof, is from about 1:10 to about 5:1.

In another embodiment, the herbicidal composition concentrate comprises:
(a) dicamba, or an agriculturally acceptable salt or ester thereof; and
(b) acetic acid, or an agriculturally acceptable salt thereof;
wherein the concentrate comprises an amount of the acetic acid, or agriculturally acceptable salt thereof, sufficient to reduce the concentration of volatilized dicamba, or agriculturally acceptable salt or ester thereof, in the vapor phase surrounding the concentrate by at least about 10%, 20%, 30%, 40%, 50%, 60%, 70%, 80%, 90%, or 95% A relative to the concentration of volatilized dicamba, or agriculturally acceptable salt or ester thereof, in the vapor phase surrounding an otherwise identical concentrate lacking the acetic acid, or agriculturally acceptable salt thereof.

In further embodiments, the herbicidal composition concentrate comprises a dicamba salt selected from the group consisting of N,N-bis-[aminopropyl]methylamine, monoethanolamine, dim ethylamine, isopropylamine, diglycolamine, potassium, and sodium salts, and combinations thereof.

In further embodiments, the herbicidal composition concentrate comprises an acetate salt. In another embodiment, the acetate salt is an alkali metal salt. In another embodiment, the acetate salt is a potassium salt. In another embodiment, the acetate salt is a sodium salt.

In further embodiments, the herbicidal composition concentrate further comprises a buffer.

In further embodiments, the herbicidal composition concentrate further comprises an alkali metal phosphate, such as dipotassium phosphate.

In further embodiments, the herbicidal composition concentrate is a dry powder herbicidal composition.

In further embodiments, the herbicidal composition concentrate is an aqueous herbicidal composition.

In further embodiments, the herbicidal composition concentrate further comprises a non-auxin herbicide. In another embodiment, the non-auxin herbicide is selected from the group consisting of acetochlor, glyphosate, glufosinate, flumioxazin, fomesafen, and agriculturally acceptable salts thereof. In another embodiment, the concentrate comprising a non-auxin herbicide satisfies one or more of the following conditions:
the sum of the concentration of auxin herbicide and the concentration of non-auxin herbicide is from about 120 grams (acid equivalent weight)/L to about 600 grams (acid equivalent weight)/L;
the acid equivalent weight ratio of auxin herbicide to non-auxin herbicide is from about 1:5 to about 2:1; and
the acid equivalent weight ratio of monocarboxylic acid, or monocarboxylate thereof, to auxin herbicide is from about 1:10 to about 5:1.

In further embodiments, the herbicidal composition concentrate has a pH greater than or equal to the $pK_a$ of acetic acid (i.e., 4.8).

4. Illustrative Composition Embodiments (Dicamba/Glyphosate Concentrate)

One embodiment of the invention is directed to a herbicidal composition concentrate comprising:

(a) dicamba, or an agriculturally acceptable salt or ester thereof;
(b) glyphosate, or an agriculturally acceptable salt thereof; and
(c) acetic acid, or an agriculturally acceptable salt thereof;
wherein the molar ratio of acetic acid, or agriculturally acceptable salt thereof, to dicamba, or agriculturally acceptable salt or ester thereof, is from about 1:10 to about 10:1.

In another embodiment, the herbicidal composition concentrate comprises:
(a) dicamba, or an agriculturally acceptable salt or ester thereof;
(b) glyphosate, or an agriculturally acceptable salt thereof; and
(c) acetic acid, or an agriculturally acceptable salt thereof;
wherein the acid equivalent weight ratio of acetic acid, or agriculturally acceptable salt thereof, to dicamba, or agriculturally acceptable salt or ester thereof, is from about 1:10 to about 5:1.

In another embodiment, the herbicidal composition concentrate comprises:
(a) dicamba, or an agriculturally acceptable salt or ester thereof;
(b) glyphosate, or an agriculturally acceptable salt thereof; and
(c) acetic acid, or an agriculturally acceptable salt thereof;
wherein the concentrate contains an amount (acid equivalent weight) of the acetic acid, or agriculturally acceptable salt thereof, from about 0.25% to about 25% by weight of the concentrate.

In another embodiment, the herbicidal composition concentrate comprises:
(a) dicamba, or an agriculturally acceptable salt or ester thereof;
(b) glyphosate, or an agriculturally acceptable salt thereof; and
(c) acetic acid, or an agriculturally acceptable salt thereof;
wherein the concentration of the acetic acid, or agriculturally acceptable salt thereof, is from about 1 gram (acid equivalent weight)/L to about 250 grams (acid equivalent weight)/L.

In another embodiment, the herbicidal composition concentrate comprises:
(a) dicamba, or an agriculturally acceptable salt or ester thereof;
(b) glyphosate, or an agriculturally acceptable salt thereof; and
(c) acetic acid, or an agriculturally acceptable salt thereof;
wherein the sum of the concentration of dicamba, or an agriculturally acceptable salt or ester thereof, and the concentration of glyphosate, or an agriculturally acceptable salt thereof, is from about 120 grams (acid equivalent weight)/L to about 600 grams (acid equivalent weight)/L. In another embodiment, the sum of the concentration of dicamba, or an agriculturally acceptable salt or ester thereof, and the concentration of glyphosate, or an agriculturally acceptable salt thereof, is from about 360 grams (acid equivalent weight)/L to about 480 grams (acid equivalent weight)/L.

In another embodiment, the herbicidal composition concentrate comprises:
(a) dicamba, or an agriculturally acceptable salt or ester thereof;
(b) glyphosate, or an agriculturally acceptable salt thereof; and
(c) acetic acid, or an agriculturally acceptable salt thereof;

wherein the sum of the concentration of dicamba, or an agriculturally acceptable salt or ester thereof, and the concentration of glyphosate, or an agriculturally acceptable salt thereof, is from about 120 grams (acid equivalent weight)/L to about 600 grams (acid equivalent weight)/L; and wherein the acid equivalent weight ratio of dicamba, or an agriculturally acceptable salt or ester thereof, to glyphosate, or an agriculturally acceptable salt thereof, is from about 1:5 to about 2:1.

In another embodiment, the herbicidal composition concentrate comprises:
(a) dicamba, or an agriculturally acceptable salt or ester thereof;
(b) glyphosate, or an agriculturally acceptable salt thereof; and
(c) acetic acid, or an agriculturally acceptable salt thereof;
wherein the sum of the concentration of dicamba, or an agriculturally acceptable salt or ester thereof, and the concentration of glyphosate, or an agriculturally acceptable salt thereof, is from about 120 grams (acid equivalent weight)/L to about 600 grams (acid equivalent weight)/L;
wherein the acid equivalent weight ratio of dicamba, or an agriculturally acceptable salt or ester thereof, to glyphosate, or an agriculturally acceptable salt thereof, is from about 1:5 to about 2:1; and
wherein the acid equivalent weight ratio of acetic acid, or agriculturally acceptable salt thereof, to dicamba, or agriculturally acceptable salt or ester thereof, is from about 1:10 to about 5:1.

In another embodiment, the herbicidal composition concentrate comprises:
(a) dicamba, or an agriculturally acceptable salt or ester thereof;
(b) glyphosate, or an agriculturally acceptable salt thereof; and
(c) acetic acid, or an agriculturally acceptable salt thereof;
wherein the concentrate comprises an amount of the acetic acid, or agriculturally acceptable salt thereof, sufficient to reduce the concentration of volatilized dicamba, or agriculturally acceptable salt or ester thereof, in the vapor phase surrounding the concentrate by at least about 10%, 20%, 30%, 40%, 50%, 60%, 70%, 80%, 90%, or 95% A relative to the concentration of volatilized dicamba, or agriculturally acceptable salt or ester thereof, in the vapor phase surrounding an otherwise identical concentrate lacking the acetic acid, or agriculturally acceptable salt thereof.

In further embodiments, the herbicidal composition concentrate comprises a dicamba salt selected from the group consisting of N,N-bis-[aminopropyl]methylamine, monoethanolamine, dimethylamine, isopropylamine, diglycolamine, potassium, and sodium salts, and combinations thereof.

In further embodiments, the herbicidal composition concentrate comprises an acetate salt. In another embodiment, the acetate salt is an alkali metal salt. In another embodiment, the acetate salt is a potassium salt. In another embodiment, the acetate salt is a sodium salt.

In further embodiments, the herbicidal composition concentrate further comprises a buffer.

In further embodiments, the herbicidal composition concentrate further comprises an alkali metal phosphate, such as dipotassium phosphate.

In further embodiments, the herbicidal composition concentrate is a dry powder herbicidal composition.

In further embodiments, the herbicidal composition concentrate is an aqueous herbicidal composition.

In another embodiment, the concentrate comprises a glyphosate salt selected from the group consisting of ammonium, diammonium, dimethylammonium, monoethanolamine, isopropylamine, and potassium salts, and combinations thereof.

In another embodiment, the concentrate satisfies one or more of the following conditions:
the sum of the concentration of dicamba, or agriculturally acceptable salt thereof, and the concentration of glyphosate, or agriculturally acceptable salt thereof, is from about 120 grams (acid equivalent weight)/L to about 600 grams (acid equivalent weight)/L;
the acid equivalent weight ratio of dicamba, or agriculturally acceptable salt thereof, to glyphosate, or agriculturally acceptable salt thereof, is from about 1:5 to about 2:1; and
the acid equivalent weight ratio of monocarboxylic acid, or monocarboxylate thereof, to dicamba, or agriculturally acceptable salt thereof, is from about 1:10 to about 5:1.

In further embodiments, the herbicidal composition concentrate has a pH greater than or equal to the $pK_a$ of acetic acid (i.e., 4.8).

5. Illustrative Composition Embodiments (Dicamba Application Mixture)

In further embodiments, the herbicidal compositions correspond to the compositions described above in the "Illustrative Composition Embodiment (Auxin Herbicide Application Mixture)" section wherein the auxin herbicide is dicamba, or an agriculturally acceptable salt or ester thereof.

6. Illustrative Composition Embodiments (Dicamba/Glyphosate Application Mixture)

In further embodiments, the herbicidal compositions correspond to the compositions described above in the "Illustrative Composition Embodiment (Auxin Herbicide Application Mixture)" section wherein the auxin herbicide is dicamba, or an agriculturally acceptable salt or ester thereof, and the compositions further comprise glyphosate, or an agriculturally acceptable salt or ester thereof.

7. Illustrative Composition Embodiments (Dicamba/Glufosinate Application Mixture)

In further embodiments, the herbicidal compositions correspond to the compositions described above in the "Illustrative Composition Embodiment (Auxin Herbicide Application Mixture)" section wherein the auxin herbicide is dicamba, or an agriculturally acceptable salt or ester thereof, and the compositions further comprise glufosinate, or an agriculturally acceptable salt or ester thereof.

8. Illustrative Composition Embodiments (2,4-D)

Compositions of particular interest also include herbicidal compositions comprising 2,4-D, or an agriculturally acceptable salt or ester thereof; acetic acid, or an agriculturally acceptable salt thereof; and, optionally, glyphosate, or an agriculturally acceptable salt thereof.

In further embodiments, the herbicidal compositions correspond to the compositions described above in the "Illustrative Composition Embodiment (Dicamba Concentrate)," "Illustrative Composition Embodiment (Dicamba/Glyphosate Concentrate)," "Illustrative Composition Embodiment (Dicamba Application Mixture)," "Illustrative Composition Embodiment (Dicamba/Glyphosate Application Mixture)" and "Illustrative Composition Embodiment (Dicamba/Glufosinate Application Mixture)" sections except that the dicamba, or agriculturally acceptable salt or ester thereof, is replaced with 2,4-D, or an agriculturally acceptable salt or ester thereof.

9. Illustrative Composition Embodiments (Dicamba Liquid Concentrate)

One embodiment of the invention is directed to a herbicidal composition that is a liquid concentrate comprising:
dicamba, or an agriculturally acceptable salt or ester thereof; and
acetic acid, or an agriculturally acceptable salt thereof; wherein:
the concentrate contains an amount (acid equivalent weight) of the acetic acid, or agriculturally acceptable salt thereof, from about 1% to about 25% by weight of the concentrate; and
the concentrate contains an amount (acid equivalent weight) of dicamba, or an agriculturally acceptable salt or ester thereof, from about 10% to about 60% by weight of the concentrate.

In one aspect, the liquid concentrate has a dicamba loading from about 300 g a.e./L to about 400 g a.e./L.

In another embodiment, the liquid concentrate comprises:
dicamba, or an agriculturally acceptable salt or ester thereof; and
acetic acid, or an agriculturally acceptable salt thereof; wherein:
the concentrate contains an amount (acid equivalent weight) of the acetic acid, or agriculturally acceptable salt thereof, from about 2% to about 20% by weight of the concentrate; and
the concentrate contains an amount (acid equivalent weight) of dicamba, or an agriculturally acceptable salt or ester thereof, from about 15% to about 50% by weight of the concentrate.

In another embodiment, the liquid concentrate comprises:
dicamba, or an agriculturally acceptable salt or ester thereof; and
acetic acid, or an agriculturally acceptable salt thereof; wherein:
the concentrate contains an amount (acid equivalent weight) of the acetic acid, or agriculturally acceptable salt thereof, from about 3% to about 15% by weight of the concentrate; and
the concentrate contains an amount (acid equivalent weight) of dicamba, or an agriculturally acceptable salt or ester thereof, from about 20% to about 40% by weight of the concentrate.

In another embodiment, the liquid concentrate comprises:
dicamba, or an agriculturally acceptable salt or ester thereof; and
acetic acid, or an agriculturally acceptable salt thereof; wherein:
the concentrate contains an amount (acid equivalent weight) of the acetic acid, or agriculturally acceptable salt thereof, from about 3% to about 10% by weight of the concentrate; and
the concentrate contains an amount (acid equivalent weight) of dicamba, or an agriculturally acceptable salt or ester thereof, from about 25% to about 35% by weight of the concentrate.

In further embodiments, the liquid concentrate comprises a dicamba salt selected from the group consisting of N,N-bis-[aminopropyl]methylamine, monoethanolamine, dimethylamine, isopropylamine, diglycolamine, potassium, and sodium salts, and combinations thereof. In one aspect, the liquid concentrate comprises a dicamba diglycolamine salt.

In further embodiments, the liquid concentrate comprises an acetate salt. In another embodiment, the acetate salt is an alkali metal salt. In another embodiment, the acetate salt is a potassium salt. In another embodiment, the acetate salt is a sodium salt.

In further embodiments, the liquid concentrate comprises an acetate salt that is formed in situ during the preparation of the liquid concentrate when acetic acid is contacted with a neutralizing base such as an alkali metal hydroxide. For example, the liquid concentrate can be prepared by mixing the dicamba, or agriculturally acceptable salt or ester thereof, with water followed by the addition of acetic acid followed by the addition of the neutralizing base. Although a specific order of addition of the ingredients is not required to prepare the final composition, the order of addition described above can be advantageous to reduce the heat generation resulting when the ingredients are combined. In one aspect, the neutralizing base is potassium hydroxide. In another aspect, the neutralizing base is sodium hydroxide.

10. Illustrative Composition Embodiments (Dicamba Dry Concentrate)

One embodiment of the invention is directed to a herbicidal composition that is a dry concentrate comprising:
dicamba, or an agriculturally acceptable salt or ester thereof; and
acetic acid, or an agriculturally acceptable salt thereof; wherein:
the concentrate contains an amount (acid equivalent weight) of the acetic acid, or agriculturally acceptable salt thereof, from about 1% to about 40% by weight of the concentrate;
the concentrate contains an amount (acid equivalent weight) of dicamba, or an agriculturally acceptable salt or ester thereof, from about 40% to about 90% by weight of the concentrate; and
wherein the sum of the acetic acid weight percent and the dicamba weight percent is less than or equal to 100%.

In another embodiment, the dry concentrate comprises:
dicamba, or an agriculturally acceptable salt or ester thereof; and
acetic acid, or an agriculturally acceptable salt thereof; wherein:
the concentrate contains an amount (acid equivalent weight) of the acetic acid, or agriculturally acceptable salt thereof, from about 3% to about 30% by weight of the concentrate;
the concentrate contains an amount (acid equivalent weight) of dicamba, or an agriculturally acceptable salt or ester thereof, from about 50% to about 80% by weight of the concentrate; and
wherein the sum of the acetic acid weight percent and the dicamba weight percent is less than or equal to 100%.

In another embodiment, the dry concentrate comprises:
dicamba, or an agriculturally acceptable salt or ester thereof; and
acetic acid, or an agriculturally acceptable salt thereof; wherein:
the concentrate contains an amount (acid equivalent weight) of the acetic acid, or agriculturally acceptable salt thereof, from about 5% to about 20% by weight of the concentrate; and
the concentrate contains an amount (acid equivalent weight) of dicamba, or an agriculturally acceptable salt or ester thereof, from about 60% to about 75% by weight of the concentrate.

In further embodiments, the dry concentrate comprises a dicamba salt selected from the group consisting of N,N-bis-

[aminopropyl]methylamine, monoethanolamine, dimethylamine, isopropylamine, diglycolamine, potassium, and sodium salts, and combinations thereof. In one aspect, the liquid concentrate comprises a dicamba diglycolamine salt.

In further embodiments, the dry concentrate comprises an acetate salt. In another embodiment, the acetate salt is an alkali metal salt. In another embodiment, the acetate salt is a potassium salt. In another embodiment, the acetate salt is a sodium salt.

In further embodiments, the dry concentrate is in the form of a dry powder.

In further embodiments, the dry concentrate is in the form of dry granules.

11. Illustrative Composition Embodiments (Dicamba/Glyphosate Liquid Premix)

One embodiment of the invention is directed to a herbicidal composition that is a liquid concentrate comprising:
  dicamba, or an agriculturally acceptable salt or ester thereof; and
  glyphosate, or an agriculturally acceptable salt thereof; and
  acetic acid, or an agriculturally acceptable salt thereof;
  wherein:
    the concentrate contains an amount (acid equivalent weight) of the acetic acid, or agriculturally acceptable salt thereof, from about 1% to about 25% by weight of the concentrate;
    the concentrate contains an amount (acid equivalent weight) of dicamba, or an agriculturally acceptable salt or ester thereof, from about 2% to about 25% by weight of the concentrate; and
    the concentrate contains an amount (acid equivalent weight) of glyphosate, or an agriculturally acceptable salt thereof, from about 4% to about 50% by weight of the concentrate.

In one aspect, the liquid concentrate has a total herbicide loading from about 350 g a.e./L to about 500 g a.e./L.

In another embodiment, the liquid concentrate comprises:
  dicamba, or an agriculturally acceptable salt or ester thereof; and
  glyphosate, or an agriculturally acceptable salt thereof; and
  acetic acid, or an agriculturally acceptable salt thereof;
  wherein:
    the concentrate contains an amount (acid equivalent weight) of the acetic acid, or agriculturally acceptable salt thereof, from about 2% to about 20% by weight of the concentrate;
    the concentrate contains an amount (acid equivalent weight) of dicamba, or an agriculturally acceptable salt or ester thereof, from about 3% to about 20% by weight of the concentrate; and
    the concentrate contains an amount (acid equivalent weight) of glyphosate, or an agriculturally acceptable salt thereof, from about 6% to about 40% by weight of the concentrate.

In another embodiment, the liquid concentrate comprises:
  dicamba, or an agriculturally acceptable salt or ester thereof; and
  glyphosate, or an agriculturally acceptable salt thereof; and
  acetic acid, or an agriculturally acceptable salt thereof;
  wherein:
    the concentrate contains an amount (acid equivalent weight) of the acetic acid, or agriculturally acceptable salt thereof, from about 3% to about 15% by weight of the concentrate;
    the concentrate contains an amount (acid equivalent weight) of dicamba, or an agriculturally acceptable salt or ester thereof, from about 4% to about 15% by weight of the concentrate; and
    the concentrate contains an amount (acid equivalent weight) of glyphosate, or an agriculturally acceptable salt thereof, from about 8% to about 30% by weight of the concentrate.

In another embodiment, the liquid concentrate comprises:
  dicamba, or an agriculturally acceptable salt or ester thereof; and
  glyphosate, or an agriculturally acceptable salt thereof; and
  acetic acid, or an agriculturally acceptable salt thereof;
  wherein:
    the concentrate contains an amount (acid equivalent weight) of the acetic acid, or agriculturally acceptable salt thereof, from about 3% to about 10% by weight of the concentrate;
    the concentrate contains an amount (acid equivalent weight) of dicamba, or an agriculturally acceptable salt or ester thereof, from about 5% to about 15% by weight of the concentrate; and
    the concentrate contains an amount (acid equivalent weight) of glyphosate, or an agriculturally acceptable salt thereof, from about 10% to about 30% by weight of the concentrate.

In further embodiments, the liquid concentrate comprises a dicamba salt selected from the group consisting of N,N-bis-[aminopropyl]methylamine, monoethanolamine, dimethylamine, isopropylamine, diglycolamine, potassium, and sodium salts, and combinations thereof. In one aspect, the liquid concentrate comprises a dicamba diglycolamine salt.

In further embodiments, the liquid concentrate comprises an acetate salt. In another embodiment, the acetate salt is an alkali metal salt. In another embodiment, the acetate salt is a potassium salt. In another embodiment, the acetate salt is a sodium salt.

In further embodiments, the liquid concentrate comprises an acetate salt that is formed in situ during the preparation of the liquid concentrate when acetic acid is contacted with a neutralizing base such as an alkali metal hydroxide. For example, the liquid concentrate can be prepared by mixing the dicamba, or agriculturally acceptable salt or ester thereof, with water followed by the addition of acetic acid followed by the addition of the neutralizing base. Although a specific order of addition of the ingredients is not required to prepare the final composition, the order of addition described above can be advantageous to reduce the heat generation resulting when the ingredients are combined. In one aspect, the neutralizing base is potassium hydroxide. In another aspect, the neutralizing base is sodium hydroxide.

12. Illustrative Composition Embodiments (Dicamba/Glyphosate Dry Premix)

One embodiment of the invention is directed to a herbicidal composition that is a dry concentrate comprising:
  dicamba, or an agriculturally acceptable salt or ester thereof; and
  glyphosate, or an agriculturally acceptable salt thereof; and
  acetic acid, or an agriculturally acceptable salt thereof;
  wherein:
    the concentrate contains an amount (acid equivalent weight) of the acetic acid, or agriculturally acceptable salt thereof, from about 1% to about 40% by weight of the concentrate;

the concentrate contains an amount (acid equivalent weight) of dicamba, or an agriculturally acceptable salt or ester thereof, from about 5% to about 40% by weight of the concentrate;

the concentrate contains an amount (acid equivalent weight) of glyphosate, or an agriculturally acceptable salt thereof, from about 40% to about 80% by weight of the concentrate; and wherein the sum of the acetic acid weight percent, the dicamba weight percent, and the glyphosate weight percent is less than or equal to 100%.

In another embodiment, the dry concentrate comprises:

dicamba, or an agriculturally acceptable salt or ester thereof; and glyphosate, or an agriculturally acceptable salt thereof; and acetic acid, or an agriculturally acceptable salt thereof; wherein:

the concentrate contains an amount (acid equivalent weight) of the acetic acid, or agriculturally acceptable salt thereof, from about 3% to about 30% by weight of the concentrate;

the concentrate contains an amount (acid equivalent weight) of dicamba, or an agriculturally acceptable salt or ester thereof, from about 10% to about 35% by weight of the concentrate; and the concentrate contains an amount (acid equivalent weight) of glyphosate, or an agriculturally acceptable salt thereof, from about 40% to about 70% by weight of the concentrate; and wherein the sum of the acetic acid weight percent, the dicamba weight percent, and the glyphosate weight percent is less than or equal to 100%.

In another embodiment, the dry concentrate comprises:

dicamba, or an agriculturally acceptable salt or ester thereof; and glyphosate, or an agriculturally acceptable salt thereof; and acetic acid, or an agriculturally acceptable salt thereof; wherein:

the concentrate contains an amount (acid equivalent weight) of the acetic acid, or agriculturally acceptable salt thereof, from about 5% to about 15% by weight of the concentrate;

the concentrate contains an amount (acid equivalent weight) of dicamba, or an agriculturally acceptable salt or ester thereof, from about 20% to about 30% by weight of the concentrate; and the concentrate contains an amount (acid equivalent weight) of glyphosate, or an agriculturally acceptable salt thereof, from about 45% to about 55% by weight of the concentrate.

In further embodiments, the dry concentrate comprises a dicamba salt selected from the group consisting of N,N-bis-[aminopropyl]methylamine, monoethanolamine, dimethylamine, isopropylamine, diglycolamine, potassium, and sodium salts, and combinations thereof. In one aspect, the liquid concentrate comprises a dicamba diglycolamine salt.

In further embodiments, the dry concentrate comprises an acetate salt. In another embodiment, the acetate salt is an alkali metal salt. In another embodiment, the acetate salt is a potassium salt. In another embodiment, the acetate salt is a sodium salt.

In further embodiments, the dry concentrate is in the form of a dry powder.

In further embodiments, the dry concentrate is in the form of dry granules.

13. Illustrative Composition Embodiments (Combination Package)

One embodiment of the invention is directed to a combination package comprising a first container comprising dicamba, or an agriculturally acceptable salt or ester thereof; and a second container comprising acetic acid, or an agriculturally acceptable salt thereof. In one aspect, the first container comprises dicamba, or an agriculturally acceptable salt or ester thereof, in an amount (acid equivalent weight) that is at least about 20% by weight of the first container. In one aspect, the first container contains a liquid composition comprising dicamba, or an agriculturally acceptable salt or ester thereof. In one aspect, the first container contains a dry composition comprising dicamba, or an agriculturally acceptable salt or ester thereof.

In another embodiment, the invention is directed to a combination package comprising a first container comprising dicamba, or an agriculturally acceptable salt or ester thereof; a second container comprising glyphosate, or an agriculturally acceptable salt thereof; and a third container comprising acetic acid, or an agriculturally acceptable salt thereof. In one aspect, the first container comprises dicamba, or an agriculturally acceptable salt or ester thereof, in an amount (acid equivalent weight) that is at least about 20% by weight of the first container. In one aspect, the first container contains a liquid composition comprising dicamba, or an agriculturally acceptable salt or ester thereof. In one aspect, the first container contains a dry composition comprising dicamba, or an agriculturally acceptable salt or ester thereof. In one aspect, the second container comprises glyphosate, or an agriculturally acceptable salt thereof, in an amount (acid equivalent weight) that is at least about 20% by weight of the second container. In one aspect, the second container contains a liquid composition comprising glyphosate, or an agriculturally acceptable salt thereof. In one aspect, the second container contains a dry composition comprising glyphosate, or an agriculturally acceptable salt thereof.

In another embodiment, the invention is directed to a combination package comprising a first container comprising dicamba, or an agriculturally acceptable salt or ester thereof; a second container comprising glufosinate, or an agriculturally acceptable salt or ester thereof; and a third container comprising acetic acid, or an agriculturally acceptable salt thereof. In one aspect, the first container comprises dicamba, or an agriculturally acceptable salt or ester thereof, in an amount (acid equivalent weight) that is at least about 20% by weight of the first container. In one aspect, the first container contains a liquid composition comprising dicamba, or an agriculturally acceptable salt or ester thereof. In one aspect, the first container contains a dry composition comprising dicamba, or an agriculturally acceptable salt or ester thereof. In one aspect, the second container comprises glufosinate, or an agriculturally acceptable salt or ester thereof, in an amount (acid equivalent weight) that is at least about 10% by weight of the second container. In one aspect, the second container contains a liquid composition comprising glufosinate, or an agriculturally acceptable salt or ester thereof. In one aspect, the second container contains a dry composition comprising glufosinate, or an agriculturally acceptable salt or ester thereof.

In another embodiment of the invention is directed to a combination package comprising a first container comprising glyphosate, or an agriculturally acceptable salt thereof; and a second container comprising acetic acid, or an agriculturally acceptable salt thereof. In one aspect, the first container comprises glyphosate, or an agriculturally acceptable salt thereof, in an amount (acid equivalent weight) that is at least about 20% by weight of the first container. In one aspect, the first container contains a liquid composition comprising glyphosate, or an agriculturally acceptable salt thereof. In one aspect, the first container contains a dry composition comprising glyphosate, or an agriculturally acceptable salt thereof.

In another embodiment of the invention is directed to a combination package comprising a first container comprising glufosinate, or an agriculturally acceptable salt or ester thereof; and a second container comprising acetic acid, or an agriculturally acceptable salt thereof. In one aspect, the first container comprises glufosinate, or an agriculturally acceptable salt thereof, in an amount (acid equivalent weight) that is at least about 10% by weight of the first container. In one aspect, the first container contains a liquid composition comprising glufosinate, or an agriculturally acceptable salt thereof. In one aspect, the first container contains a dry composition comprising glufosinate, or an agriculturally acceptable salt thereof.

H. HERBICIDAL COMPOSITION ADJUVANT

As discussed in more detail later, in certain embodiments the methods of controlling the growth of auxin-susceptible plants involve the preparation of an application mixture by combining a source of auxin herbicide (e.g., CLARITY®); a source of monocarboxylic acid, or a monocarboxylate thereof; an optional source of non-auxin herbicide (e.g., DURANGO® or POWERMAX®); and water. Another embodiment of the present invention, therefore, is directed to a herbicidal adjuvant composition comprising a monocarboxylic acid, or monocarboxylate thereof, and, optionally, an alkali metal phosphate, that can serve as the source of monocarboxylic acid, or a monocarboxylate thereof, used in the preparation of the application mixture.

In one embodiment, the adjuvant composition for use in the preparation of the herbicidal composition application mixture comprises:
(a) at least one monocarboxylic acid, or a monocarboxylate thereof; and
(b) an alkali metal phosphate;
wherein the molar ratio of monocarboxylic acid, or monocarboxylate thereof, to alkali metal phosphate is from about 1:5 to about 5:1.

In various embodiments, the adjuvant composition comprises a $C_1$-$C_6$-alkanoic acid, or an agriculturally acceptable salt thereof. In other embodiments, the adjuvant composition comprises a $C_1$-$C_5$-alkanoic acid, or an agriculturally acceptable salt thereof. In other embodiments, the adjuvant composition comprises a $C_1$-$C_4$-alkanoic acid, or an agriculturally acceptable salt thereof. In other embodiments, the adjuvant composition comprises a $C_1$-$C_3$-alkanoic acid, or an agriculturally acceptable salt thereof. In other embodiments, the adjuvant composition comprises a monocarboxylic acid is selected from the group consisting of formic acid, acetic acid, propionic acid, and benzoic acid. In other embodiments, the adjuvant composition comprises acetic acid, or an agriculturally acceptable salt thereof. In other embodiments, the adjuvant composition comprises formic acid, or an agriculturally acceptable salt thereof.

In another embodiment, the adjuvant composition for use in the preparation of the herbicidal composition application mixture comprises:
(a) at least one monocarboxylic acid, or a monocarboxylate thereof; and
(b) an alkali metal phosphate;
wherein the molar ratio of monocarboxylic acid, or monocarboxylate thereof, to alkali metal phosphate is from about 1:5 to about 5:1; and
wherein the composition contains an amount (acid equivalent weight) of the monocarboxylic acid, or monocarboxylate thereof, from about 2% to about 40% by weight of the composition.

In another embodiment, the adjuvant composition for use in the preparation of the aqueous herbicidal application mixture comprises:
(a) acetic acid, or an agriculturally acceptable salt thereof; and
(b) an alkali metal phosphate;
wherein the molar ratio of acetic acid, or agriculturally acceptable salt thereof, to alkali metal phosphate is from about 1:5 to about 5:1.

In another embodiment, the adjuvant composition for use in the preparation of the aqueous herbicidal application mixture comprises:
(a) acetic acid, or an agriculturally acceptable salt thereof; and
(b) an alkali metal phosphate;
wherein the molar ratio of acetic acid, or agriculturally acceptable salt thereof, to alkali metal phosphate is from about 1:5 to about 5:1; and
wherein the composition contains an amount (acid equivalent weight) of the acetic acid, or agriculturally acceptable salt thereof, from about 2% to about 40% by weight of the composition.

In another embodiment, the invention relates to an adjuvant composition for use in the preparation of the aqueous herbicidal application mixture, wherein the adjuvant composition comprises acetic acid, or an agriculturally acceptable salt thereof, in an amount (acid equivalent weight) of about 2% to about 75% by weight of the composition. In one aspect, the amount is from about 10% to about 75% by weight of the composition. In another aspect, the amount is from about 20% to about 75% by weight of the composition. In another aspect, the amount is from about 30% to about 75% by weight of the composition.

In various embodiments of the adjuvant composition, the composition is a dry powder composition.

In various embodiments of the adjuvant composition, the composition is a liquid composition, particularly an aqueous composition.

In various embodiments of the adjuvant composition, the composition comprises a non-ammoniated monocarboxylate or acetate salt. In other embodiments, the salt is an alkali metal salt, such as an alkali metal salt. In other embodiments, the salt is a potassium salt or a sodium salt, such as potassium acetate and sodium acetate.

In various embodiments of the adjuvant composition, the alkali metal phosphate is dipotassium phosphate.

In various embodiments of the adjuvant composition, the composition comprises potassium acetate and dipotassium phosphate.

I. METHODS OF REDUCING THE VOLATILITY OF AN AUXIN HERBICIDE

Another embodiment of the present invention is directed to a method of reducing the volatility of an auxin herbicide. The method generally comprises the step of contacting an auxin herbicide with a volatility-lowering effective amount of a monocarboxylic acid, or a monocarboxylate thereof, thereby reducing the volatility of the auxin herbicide.

In one embodiment, the contacting step satisfies at least one of the following conditions:

the molar ratio of the monocarboxylic acid, or monocarboxylate thereof, contacted with the auxin herbicide is from about 1:10 to about 10:1;

the acid equivalent weight ratio of the monocarboxylic acid, or monocarboxylate thereof, contacted with the auxin herbicide is from about 1:10 to about 5:1; and the amount of the monocarboxylic acid, or monocarboxylate thereof, contacted with the auxin herbicide is sufficient to reduce the concentration of volatilized auxin herbicide in the vapor phase by at least about 10%, 20%, 30%, 40%, 50%, 60%, 70%, 80%, 90%, or 95% relative to the concentration of volatilized auxin herbicide in the vapor phase for an auxin herbicide in the absence of the monocarboxylic acid, or monocarboxylate thereof.

Volatilization can be measured by conventional means known to those skilled in the art. In one such method, for example, a gas stream is passed over an auxin herbicide composition and the auxin herbicide volatilizes from the composition into the gas stream which is then quantitatively analyzed for auxin herbicide content by methods known in the art. In another method, an auxin herbicide composition is distilled and the distillation condensate and/or distilled composition is analyzed for auxin herbicide content. In still another method, auxin herbicide volatilization is qualitatively assessed in a plant response study on a chosen sensitive species which will be clear to one of skill in the art.

It is believed that the addition of the monocarboxylic acid, or monocarboxylate thereof, at the loading values discussed above to the herbicidal compositions of the present invention effectively reduces auxin herbicide volatility and the associated crop injury without significantly reducing auxin herbicide effectiveness.

In one embodiment, no reduction in auxin herbicide effectiveness is observed for a herbicidal composition of the present invention relative to a reference composition lacking the monocarboxylic acid, or monocarboxylate thereof, but otherwise having the same composition.

In another embodiment, the auxin herbicide effectiveness of a herbicidal composition of the present invention is at least about 80%, 85%, 90%, 95%, or 99% of the auxin herbicide effectiveness of a reference composition lacking the monocarboxylic acid, or monocarboxylate thereof, but otherwise having the same composition.

In another embodiment, a reduced rate of crop injury is observed for a herbicidal composition of the present invention relative to a reference composition lacking the monocarboxylic acid, or monocarboxylate thereof, but otherwise having the same composition.

In another embodiment, the rate of crop injury associated with a herbicidal composition of the present invention is less than about 90%, 80%, 70%, 60%, or 50% of the crop injury associated with a reference composition lacking the monocarboxylic acid, or monocarboxylate thereof, but otherwise having the same composition.

In another embodiment, a reduction in the rate of crop injury and no reduction in auxin herbicide effectiveness are observed for the herbicidal compositions of the present invention relative to a reference composition lacking the monocarboxylic acid, or monocarboxylate thereof, but otherwise having the same composition.

In another embodiment, the herbicidal composition loading of the monocarboxylic acid, or monocarboxylate thereof, is sufficient to provide both commercially acceptable weed control and a commercially acceptable rate of crop injury.

A "commercially acceptable rate of weed control" varies with the weed species, degree of infestation, environmental conditions, and the associated crop plant. Typically, commercially effective weed control is defined as least about 60%, 65%, 70%, 75%, 80%, 85%, 90%, 95% or even greater than 95%. Although it is generally preferable from a commercial viewpoint that 80 to 85% or more of the weeds be destroyed, commercially significant weed control can occur at much lower levels, particularly with some very noxious, herbicide-resistant plants. "Weed control," as used herein, refers to any observable measure of control of plant growth, which can include one or more of the actions of (1) killing, (2) inhibiting growth, reproduction or proliferation, and (3) removing, destroying, or otherwise diminishing the occurrence and activity of plants. Weed control can be measured by any of the various methods known in the art. For example, weed control can be determined as a percentage as compared to untreated plants following a standard procedure wherein a visual assessment of plant mortality and growth reduction is made by one skilled in the art specially trained to make such assessments. In another control measurement method, control is defined as an average plant weight reduction percentage between treated and untreated plants. Preferably, commercial weed control is achieved at no greater than 30 days after treatment (DAT), such as from 18 to 30 DAT.

A "commercially acceptable rate of crop injury" for the present invention likewise varies with the crop plant species. Typically, a commercially acceptable rate of crop injury is defined less than about 20%, 15%, 10% or even less than about 5%. Crop damage can be measured by any means known in the art, such as those describe above for weed control determination. Preferably, crop damage appears no more than from 10% to 20% at no greater than 30 DAT, such as from 3 to 21 or from 3 to 30 DAT.

J. METHODS OF CONTROLLING GROWTH OF AUXIN-SUSCEPTIBLE PLANTS

Another embodiment of the present invention is directed to methods of controlling the growth of auxin-susceptible plants, particularly those growing in and/or adjacent to a field of crop plants. The methods generally comprise applying to the auxin-susceptible plants an aqueous herbicidal composition mixture comprising at least one auxin herbicide; at least one monocarboxylic acid, or monocarboxylate thereof; and, optionally, a non-auxin herbicide; wherein the application mixture exhibits reduced auxin herbicide volatility relative to an otherwise identical application mixture lacking the monocarboxylic acid, or monocarboxylate thereof.

The aqueous herbicidal composition mixture applied to the auxin-susceptible plants can be provided, for example, in the following manner:

(a) as a ready-to-use aqueous herbicidal composition that can be applied without the need for further dilution with water or other preparation;

(b) as a herbicidal composition application mixture prepared by diluting with water any of the herbicidal composition concentrates within in the scope of the present disclosure;

(c) as a herbicidal composition application mixture prepared by combining two or more separate components with water (e.g., a tank mix);

(d) as a herbicidal composition application mixture prepared by introducing separate feed streams to a spraying or application system so that the feed streams are co-mixed immediately prior to use; or (e) in any other manner reasonably adapted to apply to auxin-susceptible plants a herbicidal composition comprising the auxin herbicide in admixture with the monocarboxylic acid, or monocarboxylate thereof.

In one embodiment, the methods of controlling the growth of auxin-susceptible plants comprise the steps of:

(a) preparing an aqueous herbicidal application mixture by diluting with water a herbicidal composition concentrate of any of the herbicidal composition concentrates disclosed in this application; and (b) applying a herbicidally effective amount of the application mixture to the auxin-susceptible plants.

In another embodiment, the preparing step does not comprise separately introducing a pH-lowering agent (e.g., an acidifying agent) with the concentrate and water during the preparation of the application mixture; wherein the pH-lowering agent is one that is capable of lowering the pH of the application mixture in the absence of any buffering provided by other components of the application mixture.

In one embodiment, the methods of controlling the growth of auxin-susceptible plants comprise the steps of:

(a) combining a source of auxin herbicide; a source of monocarboxylic acid, or a monocarboxylate thereof; and water to prepare an aqueous herbicidal application mixture; and (b) applying a herbicidally effective amount of the application mixture to the auxin-susceptible plants;

wherein the application mixture satisfies one or more of the following conditions:

the molar ratio of monocarboxylic acid, or monocarboxylate thereof, to auxin herbicide is from about 1:10 to about 10:1;

the acid equivalent weight ratio of monocarboxylic acid, or monocarboxylate thereof, to auxin herbicide is from about 1:10 to about 5:1;

the application mixture contains an amount (acid equivalent weight) of the monocarboxylic acid, or monocarboxylate thereof, from about 0.01% to about 25 by weight of the application mixture;

the concentration of the monocarboxylic acid, or monocarboxylate thereof, is from about 1 gram (acid equivalent weight)/L to about 250 grams (acid equivalent weight)/L; and the application mixture comprises an amount of the monocarboxylic acid, or monocarboxylate thereof, sufficient to reduce the concentration of volatilized auxin herbicide in the vapor phase surrounding the application mixture by at least about 10% relative to the concentration of volatilized auxin herbicide in the vapor phase surrounding an otherwise identical application mixture lacking the monocarboxylic acid, or monocarboxylate thereof.

In one aspect, the application mixture contains an amount (acid equivalent weight) of the monocarboxylic acid, or monocarboxylate thereof, from about 0.1% to about 25%, by weight of the application mixture.

In another embodiment, the methods of controlling the growth of auxin-susceptible plants comprise the steps of:

(a) combining a source of auxin herbicide; a source of non-auxin herbicide, or agriculturally acceptable salt thereof; a source of monocarboxylic acid, or a monocarboxylate thereof; and water to prepare an aqueous herbicidal application mixture; and (b) applying a herbicidally effective amount of the application mixture to the auxin-susceptible plants;

wherein the application mixture satisfies one or more of the following conditions:

the molar ratio of monocarboxylic acid, or monocarboxylate thereof, to auxin herbicide is from about 1:10 to about 10:1;

the acid equivalent weight ratio of monocarboxylic acid, or monocarboxylate thereof, to auxin herbicide is from about 1:10 to about 5:1;

the application mixture contains an amount (acid equivalent weight) of the monocarboxylic acid, or monocarboxylate thereof, from about 0.01% to about 25 by weight of the application mixture;

the concentration of the monocarboxylic acid, or monocarboxylate thereof, is from about 1 gram (acid equivalent weight)/L to about 250 grams (acid equivalent weight)/L; and the application mixture comprises an amount of the monocarboxylic acid, or monocarboxylate thereof, sufficient to reduce the concentration of volatilized auxin herbicide in the vapor phase surrounding the application mixture by at least about 10% relative to the concentration of volatilized auxin herbicide in the vapor phase surrounding an otherwise identical application mixture lacking the monocarboxylic acid, or monocarboxylate thereof.

In one aspect, the application mixture contains an amount (acid equivalent weight) of the monocarboxylic acid, or monocarboxylate thereof, from about 0.1% to about 25%, by weight of the application mixture.

When the methods of controlling the growth of auxin-susceptible plants involve the use of a herbicidal composition application mixture comprising a non-auxin herbicide, the application mixture generally satisfies one or more of the following conditions:

the sum of the concentration of auxin herbicide and the concentration of non-auxin herbicide is from about 1 gram (acid equivalent weight)/L to about 50 grams (acid equivalent weight)/L;

the acid equivalent weight ratio of auxin herbicide to non-auxin herbicide is from about 1:5 to about 2:1; and the acid equivalent weight ratio of monocarboxylic acid, or monocarboxylate thereof, to auxin herbicide is from about 1:10 to about 5:1.

In various embodiments of the described methods of controlling the growth of auxin-susceptible plants, the application mixture comprises a non-auxin herbicide is selected from the group consisting of acetochlor, glyphosate, glufosinate, flumioxazin, fomesafen, and agriculturally acceptable salts thereof. In one embodiment, the application mixture comprises glyphosate, or an agriculturally acceptable salt thereof. In another embodiment, the application mixture comprises glufosinate, or an agriculturally acceptable salt thereof.

In various embodiments of the described methods of controlling the growth of auxin-susceptible plants, the auxin herbicide is selected from the group consisting of dicamba, or an agriculturally acceptable salt or ester thereof, and 2,4-D, or an agriculturally acceptable salt or ester thereof.

In various embodiments of the described methods of controlling the growth of auxin-susceptible plants, the auxin herbicide is dicamba, or an agriculturally acceptable salt or ester thereof.

In various embodiments of the described methods of controlling the growth of auxin-susceptible plants, the auxin herbicide is 2,4-D, or an agriculturally acceptable salt or ester thereof.

In various embodiments of the described methods of controlling the growth of auxin-susceptible plants, the application mixture comprises a monocarboxylate salt.

In various embodiments of the described methods of controlling the growth of auxin-susceptible plants, the application mixture comprises acetic acid, or an agriculturally acceptable salt thereof.

In various embodiments of the described methods of controlling the growth of auxin-susceptible plants, the monocarboxylate or acetate salt is a non-ammoniated salt. In still other embodiments, the salt is an alkali metal salt. In still other embodiments, the salt is a potassium salt. In still other embodiments, the salt is a sodium salt.

In various embodiments of the described methods of controlling the growth of auxin-susceptible plants, the application mixture further comprises a buffer.

In various embodiments of the described methods of controlling the growth of auxin-susceptible plants, the application mixture further comprises an alkali metal phosphate, such as dipotassium phosphate.

In various embodiments of the described methods of controlling the growth of auxin-susceptible plants, the combining step does not comprise separately introducing a pH-lowering agent with the source of auxin herbicide; the source of monocarboxylic acid, or monocarboxylate thereof; and water during the preparation of the application mixture; wherein the pH-lowering agent is one that is capable of lowering the pH of the application mixture in the absence of any buffering provided by other components of the application mixture.

In various embodiments of the described methods of controlling the growth of auxin-susceptible plants wherein the application mixture comprises a non-auxin herbicide, the combining step does not comprise separately introducing a pH-lowering agent with the source of auxin herbicide; the source of non-auxin herbicide; the source of monocarboxylic acid, or monocarboxylate thereof; and water during the preparation of the application mixture; wherein the pH-lowering agent is one that is capable of lowering the pH of the application mixture in the absence of any buffering provided by other components of the application mixture.

In the described methods, the application mixture is applied to the auxin-susceptible plants at an application rate sufficient to give a commercially acceptable rate of weed control. The appropriate application rate for the application mixture can be readily determined by one of skill in the art and is usually expressed as amount of auxin herbicide per unit area treated, e.g., grams acid equivalent per hectare (g a.e./ha). Depending on the plant species and growing conditions, the period of time required to achieve a commercially acceptable rate of weed control can be as short as a week or as long as three weeks, four weeks, or one month. Typically, a period of about two to three weeks is needed for the auxin herbicide to exert its full effect.

The timing of application can vary. The application mixture can be applied, for example, pre-planting of the crop plant, such as from about two to about three weeks before planting auxin-susceptible crop plants or crop plants not having a auxin herbicide-resistant trait. Crop plants that are not susceptible to certain auxin herbicides (such as corn or plants having an auxin herbicide-resistant trait), however, generally have no pre-planting restriction and the application mixture can be applied immediately before planting such crops.

The auxin-susceptible plants can be weeds or crop plants. Crop plants include, for example, vegetable crops, grain crops, flowers, and root crops. Crop plants further encompass hybrids, inbreds, and transgenic or genetically modified plants.

In some embodiments, the crop plants are auxin tolerant species that are not susceptible to auxin herbicides or are a transgenic species that contain an auxin (e.g., dicamba) resistant trait. Examples include dicamba resistant corn, cotton or soybean. Dicamba resistant crops can further comprise one or more additional traits including, without limitation: herbicide resistance (e.g., resistance to other auxin herbicides (e.g., 2,4-D or fluoroxypyr), glyphosate, glufosinate, acetolactate synthase inhibitor herbicides (e.g., imazamox, imazethapyr, imazaquin and imazapic), acetyl CoA carboxylase inhibitors (e.g., sethoxydim and clethodim), etc.); insect resistance such as Bacillus thuringiensis (Bt); high oil; high lysine; high starch; nutritional density; and/or drought resistance.

In some embodiments, the weeds and/or crop plants are glyphosate tolerant or contain a glyphosate resistant trait. Examples include glyphosate resistant corn, cotton or soybean.

In some embodiments, the crop plants comprise stacked traits such as dicamba and glyphosate resistance; dicamba and glufosinate resistance; dicamba and acetolactate synthase (ALS) or acetohydroxy acid synthase (AHAS) resistance; dicamba, glyphosate and glufosinate resistance; dicamba, glyphosate and ALS or AHAS resistance; dicamba, glufosinate and ALS or AHAS resistance; or dicamba, glyphosate, glufosinate and ALS or AHAS resistance.

In some embodiments, the plants can additionally include other herbicide, insect and disease resistance traits, as well as combinations of those traits. For instance, the plants can have dicamba, 2,4-D, or fluoroxypyr resistant traits.

K. METHODS OF CONTROLLING OFF-SITE MOVEMENT

Another embodiment of the present invention is directed to a method of controlling off-site movement of an auxin herbicide by contacting the auxin herbicide with a volatility-lowering effective amount of a monocarboxylic acid, or a monocarboxylate thereof, prior to application of the auxin herbicide.

In one embodiment, the method comprises the steps of:
(a) preparing an aqueous herbicidal application mixture comprising an auxin herbicide; a monocarboxylic acid, or a monocarboxylate thereof; water; and, optionally, a source of non-auxin herbicide; and
(b) applying a herbicidally effective amount of the application mixture to auxin-susceptible plants;
wherein the application mixture satisfies one or more of the following conditions:
the molar ratio of monocarboxylic acid, or monocarboxylate thereof, to auxin herbicide is from about 1:10 to about 10:1;
the acid equivalent weight ratio of monocarboxylic acid, or monocarboxylate thereof, to auxin herbicide is from about 1:10 to about 5:1;
the application mixture contains an amount (acid equivalent weight) of the monocarboxylic acid, or monocarboxylate thereof, from about 0.01% to about 25 by weight of the application mixture;
the concentration of the monocarboxylic acid, or monocarboxylate thereof, is from about 1 gram (acid equivalent weight)/L to about 250 grams (acid equivalent weight)/L; and the application mixture comprises an amount of the monocarboxylic acid, or monocarboxylate thereof, sufficient to reduce the concentration of volatilized auxin herbicide in the vapor phase surrounding the application mixture by at least about 10% relative to the concentration of volatilized auxin herbicide in the vapor phase surrounding an otherwise identical application mixture lacking the monocarboxylic acid, or monocarboxylate thereof.

In one aspect, the application mixture contains an amount (acid equivalent weight) of the monocarboxylic acid, or monocarboxylate thereof, from about 0.1% to about 25%, by weight of the application mixture.

L. METHODS OF COUNSELING ON USE OF AN AUXIN HERBICIDE

Another embodiment of the present invention is directed to methods of counseling an individual regarding the preparation and/or application of an auxin herbicide.

In one embodiment, the invention is directed to a method of counseling an individual on the application of an auxin herbicide to auxin-susceptible plants, the method comprising:
(a) identifying a source of an auxin herbicide;
(b) instructing the individual to prepare an aqueous herbicidal composition application mixture from the source of auxin herbicide; and
(c) additionally instructing the individual to supplement the application mixture with a monocarboxylic acid, or monocarboxylate thereof, prior to the application of the application mixture to auxin-susceptible plants.

In another embodiment, the invention is directed to a method of counseling an individual on the application of an auxin herbicide to auxin-susceptible plants, the method comprising:
(a) identifying a source of an auxin herbicide;
(b) identifying a source of a monocarboxylic acid, or a monocarboxylate thereof; and
(c) instructing the individual to prepare an aqueous herbicidal composition application mixture from the source of auxin herbicide and the source of monocarboxylic acid, or monocarboxylate thereof, for application to the auxin-susceptible plants.

The source of monocarboxylic acid, or a monocarboxylate thereof, can be, for example, a single source such as the herbicidal composition adjuvant previously discussed, or even a source that provides for in situ formation of the monocarboxylic acid, or monocarboxylate thereof, in the herbicidal composition application mixture.

Having described the invention in detail, it will be apparent that modifications and variations are possible without departing from the scope of the invention defined in the appended claims.

M. EXAMPLES

The following non-limiting examples are provided to further illustrate the present invention. It should be noted that the composition examples below are presented on the basis of the components initially combined to form the reported tank mix or concentrate. The various embodiments of the present invention are intended to encompass such initial compositions as well as any corresponding compositions resulting from interaction among the components once combined, such as where a monocarboxylic acid salt is formed in situ by combining a monocarboxylic acid with a neutralizing base.

Example 1-A: Tank Mix Compositions (Dicamba+Glyphosate)

Unless otherwise specified, the herbicidal tank mix compositions disclosed in Examples 1-A, 1-B, and 1-C were prepared using CLARITY® (DGA dicamba from BASF), ROUNDUP POWERMAX® (potassium glyphosate from Monsanto), BANVEL® (DMA dicamba from BASF), DURANGO® DMA® (DMA glyphosate from Dow AgroSciences), LIBERTY® (ammonium glufosinate from Bayer CropScience), and/or 2,4-D amine (Albaugh) by successively adding each specified herbicide to water and mixing. Those tank mix formulations containing additional tank mix adjuvants such as potassium acetate (Sigma), dipotassium phosphate (ICL), and/or ammonium sulfate (Sigma) were typically prepared by adding aqueous stock solutions of the adjuvants to the herbicide mixture.

Herbicide salts not purchased from a commercial vendor, such as IPA glyphosate and MEA dicamba, typically were prepared by mixing the herbicide acid with the desired amine. The herbicide acid to amine ratio typically is about 1:1. In certain instances, a slight excess of amine is desired. As used in these examples, DGA refers to diglycolamine; DMA refers to dimethylamine; IPA refers to isopropylamine; and MEA refers to monoethanolamine.

Herbicidal tank mix compositions prepared by the method described above are listed in Tables 1-1 through 1-15 below:

TABLE 1-1

| (Composition 854-B) | | | |
|---|---|---|---|
| INGREDIENT | WT (g) | WT % | % ACTIVE |
| DGA dicamba (CLARITY ®) | 30.00 | 3.00% | 1.20% ae |
| ROUNDUP POWERMAX ® | 60.60 | 6.06% | 2.40% ae |
| water | 909.78 | | |

TABLE 1-2

| (Composition 854-C) | | | |
|---|---|---|---|
| INGREDIENT | WT (g) | WT % | % ACTIVE |
| DGA dicamba (CLARITY ®) | 30.03 | 3.00% | 1.20% ae |
| ROUNDUP POWERMAX ® | 60.34 | 6.03% | 2.40% ae |
| dipotassium phosphate (50%) | 40.02 | 4.00% | 2.00% |
| water | 869.74 | | |

TABLE 1-3

| (Composition 854-F) | | | |
|---|---|---|---|
| INGREDIENT | WT (g) | WT % | % ACTIVE |
| DGA dicamba (CLARITY ®) | 7.50 | 3.00% | 1.20% ae |
| ROUNDUP POWERMAX ® | 15.14 | 6.06% | 2.40% ae |
| potassium acetate | 5.04 | 2.01% | 2.01% |
| Water | 222.42 | | |

TABLE 1-4

(Composition 751-E)

| INGREDIENT | WT (g) | WT % | % ACTIVE |
|---|---|---|---|
| DGA dicamba (CLARITY ®) | 7.51 | 3.00% | 1.20% ae |
| ROUNDUP POWERMAX ® | 15.16 | 6.06% | 2.40% ae |
| ammonium sulfate (AMS) | 7.35 | 2.94% | 1.00% |
| water | 220.07 | | |

TABLE 1-5

(Composition 751-D)

| INGREDIENT | WT (g) | WT % | % ACTIVE |
|---|---|---|---|
| DGA dicamba (CLARITY ®) | 7.49 | 3.00% | 1.20% ae |
| ROUNDUP POWERMAX ® | 15.10 | 6.06% | 2.40% ae |
| potassium acetate (50%) | 10.00 | 4.00% | 2.00% |
| ammonium sulfate (34%) | 7.34 | 2.94% | 1.00% |
| water | 210.07 | | |

TABLE 1-6

(Composition 210-D)

| INGREDIENT | WT (g) | WT % | % ACTIVE |
|---|---|---|---|
| DGA dicamba (CLARITY ®) | 7.48 | 3.00% | 1.20% ae |
| ROUNDUP POWERMAX ® | 14.99 | 6.00% | 2.40% ae |
| 1:1 wt/wt 50% potassium acetate/ 50% dipotassium phosphate | 10.00 | 4.00% | 2.00% |
| water | 217.42 | | |

TABLE 1-7

(Composition 870-A)

| INGREDIENT | WT (g) | WT % | % ACTIVE |
|---|---|---|---|
| DMA glyphosate (DURANGO ® DMA ®) | 15.04 | 6.02% | 2.40% ae |
| 2,4-D amine | 15.50 | 6.20% | 2.40% ae |
| water | 219.54 | | |

TABLE 1-8

(Composition 870-B)

| INGREDIENT | WT (g) | WT % | % ACTIVE |
|---|---|---|---|
| DMA glyphosate (DURANGO ® DMA ®) | 15.04 | 6.02% | 2.40% ae |
| 2,4-D amine | 15.43 | 6.17% | 2.40% ae |
| potassium acetate (50%) | 10.02 | 4.00% | 2.00% |
| water | 209.57 | | |

TABLE 1-9

(Composition 870-C)

| INGREDIENT | WT (g) | WT % | % ACTIVE |
|---|---|---|---|
| IPA glyphosate (30.8% ae) | 19.54 | 7.82% | 2.40% ae |
| 2,4-D amine | 15.42 | 6.17% | 2.40% ae |
| potassium acetate (50%) | 10.00 | 4.00% | 2.00% |
| water | 205.04 | | |

TABLE 1-10

(Composition 870-D)

| INGREDIENT | WT (g) | WT % | % ACTIVE |
|---|---|---|---|
| IPA glyphosate (30.8%) | 19.54 | 7.82% | 2.40% ae |
| 2,4-D amine | 15.42 | 6.17% | 2.40% ae |
| water | 215.04 | | |

TABLE 1-11

(Composition 563-2)

| INGREDIENT | WT (g) | WT % | % ACTIVE |
|---|---|---|---|
| BANVEL ® | 7.34 | 2.94% | 1.20% ae |
| ROUNDUP POWERMAX ® | 15.00 | 6.00% | 2.40% ae |
| water | 227.66 | | |

TABLE 1-12

(Composition 563-5)

| INGREDIENT | WT (g) | WT % | % ACTIVE |
|---|---|---|---|
| BANVEL ® | 7.34 | 2.94% | 1.20% ae |
| ROUNDUP POWERMAX ® | 15.07 | 6.00% | 2.40% ae |
| potassium acetate (50%) | 10.05 | 4.00% | 2.00% |
| water | 217.65 | | |

TABLE 1-13

(Composition 563-1)

| INGREDIENT | WT (g) | WT % | % ACTIVE |
|---|---|---|---|
| MEA dicamba (62.2%) | 4.81 | 1.93% | 1.20% ae |
| ROUNDUP POWERMAX ® | 15.00 | 6.00% | 2.40% ae |
| water | 230.18 | | |

TABLE 1-14

(Composition 563-4)

| INGREDIENT | WT (g) | WT % | % ACTIVE |
|---|---|---|---|
| MEA dicamba (62.2%) | 4.85 | 1.93% | 1.20% ae |
| ROUNDUP POWERMAX ® | 14.96 | 6.00 | 2.40% ae |
| potassium acetate (50%) | 10.03 | 4.00% | 2% |
| water | 220.18 | | |

TABLE 1-15

(Composition 836-1)

| INGREDIENT | WT (g) | WT % | % ACTIVE |
|---|---|---|---|
| CLARITY ® | 6.01 | 3.0 | 1.2% ae |
| ROUNDUP POWERMAX ® | 12.05 | 6.1 | 2.4% ae |
| water | 181.98 | | |

For the tank mix compositions in Table 1-16 through Table 1-19, the monocarboxylic acid salt (e.g., potassium acetate) was formed in situ by combining a monocarboxylic acid with a neutralizing base. The compositions were prepared by mixing the herbicide(s) with water followed by addition of the monocarboxylic acid followed by addition of the neutralizing base. Although a specific order of addition of the ingredients is not required to prepare the final composition, the order of addition described above can be advantageous to reduce the heat generation resulting when the ingredients are combined. The neutralizing base (potassium hydroxide in the compositions below) was added as a 45% w/w aqueous solution.

TABLE 1-16

(Composition 836-2)

| INGREDIENT | WT (g) | WT % | % ACTIVE |
|---|---|---|---|
| CLARITY ® | 6.00 | 3.0 | 1.2% ae |
| ROUNDUP POWERMAX ® | 12.04 | 6.0 | 2.4% ae |
| succinic acid | 2.57 | 1.3 | |
| potassium hydroxide (45% solution) | 5.46 | | |
| water | 174.01 | | |

TABLE 1-17

(Composition 836-3)

| INGREDIENT | WT (g) | WT % | % ACTIVE |
|---|---|---|---|
| CLARITY ® | 6.00 | 3.0 | 1.2% ae |
| ROUNDUP POWERMAX ® | 12.09 | 6.0 | 2.4% ae |
| propionic acid | 1.63 | 0.8 | |
| potassium hydroxide (45% solution) | 2.72 | | |
| water | 177.65 | | |

TABLE 1-18

(Composition 836-4)

| INGREDIENT | WT (g) | WT % | % ACTIVE |
|---|---|---|---|
| CLARITY ® | 6.01 | 3.0 | 1.2% ae |
| ROUNDUP POWERMAX ® | 12.03 | 6.0 | 2.4% ae |
| acetic acid | 1.32 | 0.7 | |
| potassium hydroxide (45% solution) | 2.73 | | |
| water | 177.98 | | |

TABLE 1-19

(Composition 836-5)

| INGREDIENT | WT (g) | WT % | % ACTIVE |
|---|---|---|---|
| CLARITY ® | 6.05 | 3.0 | 1.2% ae |
| ROUNDUP POWERMAX ® | 12.03 | 6.0 | 2.4% ae |
| formic acid | 1.00 | 0.5 | |
| potassium hydroxide (45% solution) | 2.73 | | |
| Water | 178.32 | | |

TABLE 1-20

(Composition 836-6)

| INGREDIENT | WT (g) | WT % | % ACTIVE |
|---|---|---|---|
| CLARITY ® | 6.01 | 3.0 | 1.2% ae |
| ROUNDUP POWERMAX ® | 12.03 | 6.0 | 2.4% ae |
| potassium hydroxide (45% solution) | 1.78 | 0.9 | |
| water | 180.19 | | |

TABLE 1-21

(Composition 893-A)

| INGREDIENT | WT (g) | WT % | % ACTIVE |
|---|---|---|---|
| CLARITY ® | 7.50 | 3.0 | 1.2% ae |
| ROUNDUP POWERMAX ® | 15.20 | 6.0 | 2.4% ae |
| water | 227.46 | | |

TABLE 1-22

(Composition 893-B)

| INGREDIENT | WT (g) | WT % | % ACTIVE |
|---|---|---|---|
| CLARITY ® | 7.50 | 3.0 | 1.2% ae |
| ROUNDUP POWERMAX ® | 15.04 | 6.0 | 2.4% ae |
| potassium acetate (50% solution) | 10.04 | | 2.0% ai |
| water | 217.44 | | |

TABLE 1-23

(Composition 893-C)

| INGREDIENT | WT (g) | WT % | % ACTIVE |
|---|---|---|---|
| CLARITY ® | 7.67 | 3.0 | 1.2% ae |
| ROUNDUP POWERMAX ® | 15.02 | 6.0 | 2.4% ae |
| potassium formate | 5.05 | | 2.0% ai |
| water | 222.46 | | |

TABLE 1-24

(Composition 893-D)

| INGREDIENT | WT (g) | WT % | % ACTIVE |
|---|---|---|---|
| CLARITY ® | 7.51 | 3.0 | 1.2% ae |
| ROUNDUP POWERMAX ® | 15.03 | 6.0 | 2.4% ae |
| potassium benzoate | 5.05 | | 2.0% ai |
| water | 222.45 | | |

TABLE 1-25

(Composition 893-F)

| INGREDIENT | WT (g) | WT % | % ACTIVE |
|---|---|---|---|
| CLARITY ® | 7.51 | 3.0 | 1.2% ae |
| ROUNDUP POWERMAX ® | 15.04 | 6.0 | 2.4% ae |
| sodium acetate | 5.01 | | 2.0% ai |
| water | 222.44 | | |

TABLE 1-26

(Composition 854-A)

| INGREDIENT | WT (g) | WT % | % ACTIVE |
|---|---|---|---|
| CLARITY ® | 30.0 | 3.0 | 1.2% ae |
| water | | | |

TABLE 1-27

(Composition 854-D)

| INGREDIENT | WT (g) | WT % | % ACTIVE |
|---|---|---|---|
| CLARITY ® | 7.5 | 3.0 | 1.2 ae |
| ROUNDUP POWERMAX ® | 15.08 | 6.0 | 2.4 ae |
| potassium oxalate (25% solution) | 20.0 | 8.0 | 2.0 ai |
| water | 207.42 | | |

TABLE 1-28

(Composition 854-E)

| INGREDIENT | WT (g) | WT % | % ACTIVE |
|---|---|---|---|
| CLARITY ® | 7.5 | 3.0 | 1.2 ae |
| ROUNDUP POWERMAX ® | 15.08 | 6.0 | 2.4 ae |
| potassium citrate (50%) | 10.0 | 4.0 | |
| water | 217.42 | | |

TABLE 1-29

(Composition 268-1)

| INGREDIENT | WT (g) | WT % | % ACTIVE |
|---|---|---|---|
| DGA dicamba (CLARITY ®) | 6.13 | 3.05 | 1.20 ae |
| ammonium glyphosate (ROUNDUP ® ENERGY) | 7.10 | 3.53 | 2.40 ae |
| water | 186.78 | 93.422 | |

* ROUNDUP ® ENERGY is the glyphosate ammonium salt, sold as water soluble granules in Europe.

TABLE 1-30

(Composition 268-2)

| INGREDIENT | WT (g) | WT % | % ACTIVE |
|---|---|---|---|
| DGA dicamba (CLARITY ®) | 6.09 | 3.05 | 1.20 ae |
| ammonium glyphosate (ROUNDUP ® ENERGY) | 7.09 | 3.53 | 2.40 ae |
| dipotassium phosphate | 9.12 | 4.56 | 3.00 |
| water | 177.72 | 88.86 | |

TABLE 1-31

(Composition 268-3)

| INGREDIENT | WT (g) | WT % | % ACTIVE |
|---|---|---|---|
| DGA dicamba (CLARITY ®) | 6.09 | 3.05 | 1.20 ae |
| ammonium glyphosate (ROUNDUP ® ENERGY) | 7.10 | 3.53 | 2.40 ae |
| potassium acetate | 7.99 | 4.00 | 4.00 |
| water | 178.78 | 89.42 | |

TABLE 1-32

(Composition 268-4)

| INGREDIENT | WT (g) | WT % | % ACTIVE |
|---|---|---|---|
| DGA dicamba (CLARITY ®) | 6.25 | 3.05 | 1.20 ae |
| ammonium glyphosate (ROUNDUP ® ENERGY) | 7.09 | 3.53 | 2.40 ae |
| potassium acetate | 8.00 | 16.01 | 4.00 |
| water | 170.81 | 85.42 | |

TABLE 1-33

(Composition 268-5)

| INGREDIENT | WT (g) | WT % | % ACTIVE |
|---|---|---|---|
| DGA dicamba (CLARITY ®) | 6.09 | 3.05 | 1.20 ae |
| ammonium glyphosate (ROUNDUP ® ENERGY) | 7.07 | 3.53 | 2.40 ae |
| potassium acetate | 8.02 | 4.00 | 2.00 |
| dipotassium phosphate | 9.08 | 4.56 | 3.00 |
| water | 169.69 | 84.86 | |

TABLE 1-34

(Composition 268-6)

| INGREDIENT | WT (g) | WT % | % ACTIVE |
|---|---|---|---|
| DGA dicamba (CLARITY ®) | 6.11 | 3.05 | 1.20 ae |
| ROUNDUP POWERMAX ® | 12.00 | 6.00 | 2.40 ae |
| water | 181.90 | 90.95 | |

Example 1-B: Tank Mix Compositions (Dicamba+Glufosinate)

TABLE 1-35

(Composition 364-2)

| INGREDIENT | WT (g) | WT % | % ACTIVE |
|---|---|---|---|
| DGA dicamba (CLARITY ®) | 6.04 | 6.04 | 1.2% ae |
| ammonium glufosinate (LIBERTY ®) | 7.59 | 7.59 | 3.36% v/v |
| water | 186.57 | 186.57 | |

TABLE 1-36

(Composition 364-3)

| INGREDIENT | WT (g) | WT % | % ACTIVE |
|---|---|---|---|
| DGA dicamba (CLARITY ®) | 6.05 | 6.05 | 1.2% ae |
| ammonium glufosinate (LIBERTY ®) | 7.41 | 7.41 | 3.36% v/v |
| dipotassium phosphate (50%) | 9.19 | 9.19 | 3.00% v/v |
| water | 177.40 | 177.40 | |

TABLE 1-37

(Composition 364-5)

| INGREDIENT | WT % | % ACTIVE |
|---|---|---|
| DGA dicamba (CLARITY ®) | 2.9 | 1.2% ae |
| potassium hydroxide | 0.38 | |
| acetic acid | 0.23 | |
| ammonium glufosinate (LIBERTY ®) | 3.7 | 3.36% v/v |
| water | 92.79 | |

TABLE 1-38

(Composition 364-6)

| INGREDIENT | WT % | % ACTIVE |
|---|---|---|
| DGA dicamba (CLARITY ®) | 2.9 | 1.2% ae |
| potassium hydroxide | 0.38 | |
| acetic acid | 0.23 | |

TABLE 1-38-continued (Composition 364-6)

| INGREDIENT | WT % | % ACTIVE |
|---|---|---|
| ammonium glufosinate (LIBERTY ®) | 3.7 | 3.36% v/v |
| dipotassium phosphate | 4.6 | 3.00% v/v |
| water | 88.19 | |

Example 1-C: Tank Mix Compositions (Dicamba)

TABLE 1-39

(Composition 364-1)

| INGREDIENT | WT (g) | WT % | % ACTIVE |
|---|---|---|---|
| DGA dicamba (CLARITY ®) | 6.00 | 6.00 | 1.20% ae |
| water | 194.00 | 194.00 | |

TABLE 1-40

(Composition 364-4)

| INGREDIENT | WT % | % ACTIVE |
|---|---|---|
| DGA dicamba (CLARITY ®) | 2.9 | 1.2% ae |
| potassium hydroxide | 0.38 | |
| acetic acid | 0.23 | |
| water | 96.45 | |

The compositions shown in Tables 1-37, 1-38, and 1-40 above (Compositions 364-5, 364-6, and 364-4, respectively) were prepared by combining the appropriate amount of the composition shown in Table 2-17 below (Composition 871-5) with the additional components and an amount of water sufficient to provide a final dicamba concentration of 1.2% ae.

Example 1-D: Acetic Acid Adjuvant

An example of an acetic acid adjuvant for use in the preparation of a dicamba tank mix is described in Table 1-41 below.

TABLE 1-41

Adjuvant (Composition 828-2)

| INGREDIENT | WT (g) | WT % |
|---|---|---|
| potassium acetate | 25.04 | 25.0 |
| potassium citrate (monohydrate) | 24.98 | 25.0 |
| water | 50.02 | 50.0 |
| total | 100.04 | 100.0 |

Example 2-A: Liquid Concentrate Compositions (Dicamba)

Liquid concentrate compositions are described in Examples 2-A, 2-B, 2-C, and 2-D.

The potassium acetate used in the compositions in Tables 2A-1-29 through Table 2A-1-32 was prepared by adding the desired amount of glacial acetic acid to the desired amount of potassium hydroxide (45% w/w solution) in an ice bath without allowing the temperature of the solution to rise above 60° C. The pre-formed potassium acetate was then added to the solution containing the herbicide(s). The ratio indicated in the tables below is on a molar basis. For example, "50/50 AcOH/KOH" means a 1:1 M ratio of acetic acid to potassium hydroxide. The compositions in the tables below were prepared by adding the desired amount of each ingredient and stirring for about 20 minutes.

Alternatively, the monocarboxylic acid salt can be prepared by adding the monocarboxylic acid to the solution containing the herbicide(s) followed by addition of a neutralizing base. Although a specific order of addition of the ingredients is not required to prepare the final composition, the order of addition described above can be advantageous to reduce the heat generation resulting when the ingredients are combined.

TABLE 2A-1-29

(Composition 503-1)

| INGREDIENT | WT (g) | WT % | % ACTIVE |
|---|---|---|---|
| CLARITY ® | 157.4 | 78.7 | 31.0 |
| 50/50 AcOH/KOH | 42.6 | 21.3 | 6.9 (AcOH) |

TABLE 2A-1-30

(Composition 503-3)

| INGREDIENT | WT (g) | WT % | % ACTIVE |
|---|---|---|---|
| CLARITY ® | 157.4 | 78.7 | 31.0 |
| 60/40 AcOH/KOH | 42.6 | 21.3 | 8.2 (AcOH) |

TABLE 2A-1-31

(Composition 295-3)

| INGREDIENT | WT (g) | WT % | % ACTIVE |
|---|---|---|---|
| DGA dicamba (55.2%) | 112.3 | 56.2 | 31.0 |
| 60/40 AcOH/KOH | 65.1 | 32.6 | 12.6 (AcOH) |
| water | 22.6 | 11.3 | |

TABLE 2A-1-32

(Composition 295-6)

| INGREDIENT | WT (g) | WT % | % ACTIVE |
|---|---|---|---|
| DGA dicamba (55.2%) | 112.3 | 56.2 | 31.0 |
| 60/40 AcOH/KOH | 86.8 | 43.4 | 16.8 (AcOH) |
| water | 0.9 | 0.4 | |

TABLE 2A-1-33

(Composition 771-C)

| INGREDIENT | WT (g) | WT % | % ACTIVE |
|---|---|---|---|
| CLARITY ® | 29.15 | 62.94 | |
| acetic acid | 6.26 | 6.26 | |
| potassium hydroxide | 8.72 | 8.72 | |
| water | 2.19 | 2.19 | |

TABLE 2A-1-34

(Composition 761-B)

| INGREDIENT | WT (g) | WT % | % ACTIVE |
|---|---|---|---|
| CLARITY ® | 32.82 | 71.20 | |
| acetic acid | 4.48 | 9.72 | |
| potassium hydroxide | 6.24 | 13.53 | |
| water | 2.56 | | |

Example 2-B: Liquid Concentrate Compositions (Dicamba+Glyphosate)

Herbicidal compositions containing DGA dicamba and MEA glyphosate were prepared by mixing CLARITY® with MEA glyphosate with water. After stirring the mixture for five minutes, surfactants AGM550 and Agnique PG8107-G were added followed by ferric citrate (for mitigating necrosis in certain crops) and anti-foaming agent SAG 1572, and the mixture stirred for an additional 30 minutes. Premix compositions which also contain additional adjuvants, such as potassium acetate, were prepared as described above with the modification of replacing the water with the desired amount of aqueous adjuvant. The MEA glyphosate salt used in the preparation of the compositions was prepared by mixing glyphosate acid and 1.35 molar equivalents of MEA with water. The list of ingredients of the dicamba/glyphosate premix composition is set forth in Table 2-1.

TABLE 2-1

(DGA Dicamba/MEA Glyphosate Premix)

| INGREDIENT | WT (g) | WT % | % ACTIVE |
|---|---|---|---|
| DGA dicamba (CLARITY ®) | 32.36 | 32.36% | 12.75% |
| 1.35 MEA glyphosate (46.9%) | 54.37 | 54.37% | 25.50% |
| AGM 550 | 2.50 | 2.50% | |
| Agnique PG8107-G | 5.00 | 5.00% | |
| SAG 1572 | 0.01 | 0.01% | |
| Ferric citrate (7.0% Fe) | 0.31 | 0.31% | 0.02% |
| water | 5.44 | 5.44% | |

Dicamba/glyphosate premixes containing additional adjuvants, such as potassium acetate, typically were prepared by adding the desired amount of an aqueous solution of the adjuvant to the premix prepared as described in Tables 2-2 and 2-3 below.

TABLE 2-2

(Composition 751-F)

| INGREDIENT | WT (g) | WT % | % ACTIVE |
|---|---|---|---|
| DGA dicamba/MEA glyphosate premix | 23.51 | 9.40% | 1.20% ae |
| potassium acetate (50%) | 10.00 | 4.00% | 2.00% |
| water | 216.48 | | |

TABLE 2-3

(Composition 210-F)

| INGREDIENT | WT (g) | WT % | % ACTIVE |
|---|---|---|---|
| DGA dicamba/MEA glyphosate premix | 23.48 | 9.39% | 2.40% ae |
| 1:1 wt/wt 50% potassium acetate/50% dipotassium phosphate | 10.04 | 4.00% | 2.00% |
| Water | 216.51 | | |

TABLE 2-4

(Composition 210-E)

| INGREDIENT | WT (g) | WT % | % ACTIVE |
|---|---|---|---|
| DGA dicamba (CLARITY ®) | 32.2 | 32.12 | 12.75 |
| 1.35 MEA glyphosate (46.8%) | 55.0 | 54.49 | 25.50 |
| AGM 550 | 2.50 | 2.50 | |
| Agnique PG8107-G | 5.1 | 5.00 | |
| SAG 1572 | 0.02 | 0.01 | |
| Ferric citrate (7.0% Fe) | 0.33 | 0.31 | 0.02% |
| 50% K acetate solution | 5.7 | 5.7 | |

The potassium acetate used in the formulations in Tables 2-5 through Table 2-13 was prepared by adding the desired amount of glacial acetic acid to the desired amount of potassium hydroxide (45% w/w solution) in an ice bath without allowing the temperature of the solution to rise above 60° C. The ratio indicated in the tables below is on a molar basis. For example "50/50 AcOH/KOH" means a 1:1 M ratio of acetic acid to potassium hydroxide. The compositions in the tables below were prepared by adding the desired amount of each ingredient and stirring for about 20 minutes. Alternatively, the monocarboxylic acid salt can be prepared by adding the monocarboxylic acid to the solution containing the herbicide(s) followed by addition of a neutralizing base.

The Fe dopant in Tables 2-8 through 2-13 (added to mitigate necrosis in certain crops) was prepared by mixing ferric sulfate and citric acid.

TABLE 2-5

(Composition 287-5)

| INGREDIENT | WT (g) | WT % | % ACTIVE |
|---|---|---|---|
| DGA dicamba (54.8% ae) | 18.25 | 18.25 | 10.0 |
| 1.35 MEA glyphosate (46.9% ae) | 42.74 | 42.74 | 20.0 |
| SAG 1572 | 0.01 | 0.01 | |
| Ferric Citrate (7.0% Fe) | 0.31 | 0.31 | 0.02 |
| 60/40 AcOH/KOH (38.7 AcOH) | 6.98 | 6.98 | 2.70 |
| water | 31.72 | 31.72 | |

TABLE 2-6

(Composition 287-6)

| INGREDIENT | WT (g) | WT % | % ACTIVE |
|---|---|---|---|
| DGA dicamba (54.8% ae) | 17.34 | 17.34 | 9.50 |
| 1.35 MEA glyphosate (46.9% ae) | 40.60 | 40.60 | 19.00 |
| SAG 1572 | 0.01 | 0.01 | |
| Ferric Citrate (7.0% Fe) | 0.31 | 0.31 | 0.02 |
| 60/40 AcOH/KOH (38.7 AcOH) | 13.44 | 13.44 | 5.20 |
| Water | 28.30 | 28.30 | |

TABLE 2-7

(Composition 512-1)

| INGREDIENT | WT (g) | WT % | % ACTIVE |
|---|---|---|---|
| DGA dicamba (CLARITY ®) | 31.61 | 31.61 | 12.55 |
| 1.35 MEA glyphosate (46.9% ae) | 53.63 | 53.63 | 25.10 |
| AGM 550 | 2.50 | 2.50 | |
| AGNIQUE PG8107-G | 5.00 | 5.00 | |
| SAG 1572 | 0.01 | 0.01 | |
| Ferric Citrate (7.0% Fe) | 0.31 | 0.31 | 0.02 |
| 70/30 AcOH/KOH (38.7 AcOH) | 6.93 | 6.93 | |

TABLE 2-8

(Composition 248-1)

| INGREDIENT | WT (g) | WT % | % ACTIVE |
|---|---|---|---|
| DGA dicamba (55.2%) | 18.03 | 18.03 | 9.95 |
| 1.35 MEA glyphosate (46.8% ae) | 45.51 | 45.51 | 19.90 |
| Ethoquad C12 75 DEG | 3.49 | 3.49 | |
| SAG 1572 | 0.01 | 0.01 | |
| Fe Dopant (4.5% Fe) | 0.49 | 0.49 | 0.02 |
| 60/40 AcOH/KOH (38.7 AcOH) | 6.95 | 6.95 | 2.70 |
| water | 28.49 | 28.49 | |

TABLE 2-9

(Composition 248-2)

| INGREDIENT | WT (g) | WT % | % ACTIVE |
|---|---|---|---|
| DGA dicamba (55.2%) | 18.08 | 18.08 | 9.95 |
| 1.35 MEA glyphosate (46.8% ae) | 42.62 | 42.62 | 19.90 |
| Ethoquad C12 75 DEG | 3.49 | 3.49 | |
| SAG 1572 | 0.02 | 0.02 | |
| Fe Dopant (4.5% Fe) | 0.49 | 0.49 | 0.02 |
| 60/40 AcOH/KOH (38.7 AcOH) | 10.86 | 10.86 | 4.20 |
| Water | 24.61 | 24.61 | |

TABLE 2-10

(Composition 248-3)

| INGREDIENT | WT (g) | WT % | % ACTIVE |
|---|---|---|---|
| DGA dicamba (55.2%) | 17.91 | 17.91 | 9.90 |
| 1.35 MEA glyphosate (46.8% ae) | 42.28 | 42.28 | 19.80 |
| Ethoquad C12 75 DEG | 3.61 | 3.61 | |
| SAG 1572 | 0.02 | 0.02 | |
| Fe Dopant (4.5% Fe) | 0.53 | 0.53 | 0.02 |
| 60/40 AcOH/KOH (38.7 AcOH) | 13.95 | 13.95 | 5.40 |
| water | 21.81 | 21.81 | |

TABLE 2-11

(Composition 249-1)

| INGREDIENT | WT (g) | WT % | % ACTIVE |
|---|---|---|---|
| DGA dicamba (55.2%) | 18.00 | 18.00 | 9.95 |
| 1.35 MEA glyphosate (46.8% ae) | 42.52 | 42.52 | 19.90 |
| AGM 550 | 2.48 | 2.48 | |
| Agnique PG8107-G | 1.95 | 1.95 | |
| SAG 1572 | 0.01 | 0.01 | |
| Fe Dopant (4.5% Fe) | 0.60 | 0.60 | 0.02 |
| 60/40 AcOH/KOH (38.7 AcOH) | 6.96 | 6.96 | 2.70 |
| water | 27.48 | 27.48 | |

TABLE 2-12

(Composition 249-2)

| INGREDIENT | WT (g) | WT % | % ACTIVE |
|---|---|---|---|
| DGA dicamba (55.2%) | 18.04 | 18.04 | 9.95 |
| 1.35 MEA glyphosate (46.8% ae) | 42.50 | 42.50 | 19.90 |
| AGM 550 | 2.50 | 2.50 | |
| Agnique PG8107-G | 2.00 | 2.00 | |
| SAG 1572 | 0.01 | 0.01 | |
| Fe Dopant (4.5% Fe) | 0.49 | 0.49 | 0.02 |
| 60/40 AcOH/KOH (38.7 AcOH) | 10.83 | 10.83 | 4.20 |
| water | 23.59 | 23.59 | |

TABLE 2-13

(Composition 249-3)

| INGREDIENT | WT (g) | WT % | % ACTIVE |
|---|---|---|---|
| DGA dicamba (55.2%) | 17.93 | 17.93 | 9.90 |
| 1.35 MEA glyphosate (46.8% ae) | 42.37 | 42.37 | 19.80 |
| AGM 550 | 2.50 | 2.50 | |
| Agnique PG8107-G | 1.97 | 1.97 | |
| SAG 1572 | 0.01 | 0.01 | |
| Fe Dopant (4.5% Fe) | 0.49 | 0.49 | 0.02 |
| 60/40 AcOH/KOH (38.7 AcOH) | 14.00 | 14.00 | 5.40 |
| water | 20.79 | 20.79 | |

TABLE 2-14

(Composition 530-2)

| INGREDIENT | WT (g) | WT % | % ACTIVE |
|---|---|---|---|
| CLARITY ® | 125.63 | 25.13 | 9.90 ae |
| 1.35 MEA glyphosate (46.8% ae) | 211.54 | 42.31 | 19.80 ae |
| AGM 550 | 12.50 | 2.50 | |
| Agnique PG8107-G | 10.00 | 2.00 | |
| SAG 1572 | 0.05 | 0.01 | |
| Fe Dopant (4.5% Fe) | 1.94 | 0.39 | 0.02 |
| 65/35 AcOH/KOH (38.7 AcOH) | 64.29 | 12.86 | 5.40 |
| water | 199.68 | | |

TABLE 2-15

(Composition 540-1)

| INGREDIENT | WT (g) | WT % | % ACTIVE |
|---|---|---|---|
| CLARITY ® (39.4% a.e.) | 124.37 | 24.87 | 9.80 ae |
| 1.35 MEA glyphosate (46.8% ae) | 209.40 | 41.88 | 19.60 ae |
| Ethoquad C12 75 DEG | 17.50 | 3.50 | |
| 65/35 AcOH/KOH (42.0% AcOH) | 64.29 | 12.86 | 5.40 |
| Fe Dopant (4.5% Fe) | 1.94 | 0.39 | 0.0175 |
| SAG 1572 | 0.05 | 0.01 | |
| water | 82.45 | 16.49 | |

TABLE 2-16

(Composition 540-4)

| INGREDIENT | WT (g) | WT % | % ACTIVE |
|---|---|---|---|
| CLARITY ® (39.4% α.ε.) | 123.10 | 24.62 | 9.70 ae |
| 1.35 MEA glyphosate (46.8% ae) | 207.26 | 41.45 | 19.40 ae |
| AGM 550 | 12.50 | 2.50 | |
| Agnique PG8107-G | 10.00 | 2.00 | |

TABLE 2-16-continued (Composition 540-4)

| INGREDIENT | WT (g) | WT % | % ACTIVE |
|---|---|---|---|
| SAG 1572 | 0.05 | 0.01 | |
| Fe Dopant (4.5% Fe) | 1.94 | 0.39 | 0.0175 |
| 60/40 AcOH/KOH (38.7% AcOH) | 69.77 | 13.95 | 5.40 |
| Phosphate ester | 5.00 | 1.000 | |
| water | 70.38 | 14.08 | |

Example 2-C: Liquid Concentrate Compositions (Dicamba)

TABLE 2-17

(Composition 871-5)

| INGREDIENT | WT (g) | WT % | % ACTIVE |
|---|---|---|---|
| DGA dicamba (CLARITY ®) | 73.43 | 73.43 | 29.00 |
| potassium hydroxide | 9.50 | 9.50 | |
| acetic acid | 5.91 | 5.91 | |
| water | 11.16 | 11.16 | |

TABLE 2-18

(Composition 871-4)

| INGREDIENT | WT (g) | WT % | % ACTIVE |
|---|---|---|---|
| DGA dicamba (CLARITY ®) | 73.49 | 73.49 | 29.03 |
| potassium hydroxide | 9.00 | 9.00 | |
| acetic acid | 5.93 | 5.93 | |
| water | 11.58 | 11.58 | |

TABLE 2-19

(Composition 871-12)

| INGREDIENT | WT (g) | WT % | % ACTIVE |
|---|---|---|---|
| DGA dicamba (CLARITY ®) | 72.53 | 72.53 | 28.65 |
| potassium hydroxide | 13.25 | 13.25 | |
| acetic acid | 7.65 | 7.65 | |
| water | 6.57 | 6.57 | |

TABLE 2-20

(Composition 761-2)

| INGREDIENT | WT (g) | WT % | % ACTIVE |
|---|---|---|---|
| DGA dicamba (CLARITY ®) | 72.47 | 72.47 | 28.63 |
| potassium hydroxide | 13.53 | 13.53 | |
| acetic acid | 9.72 | 9.72 | |
| water | 4.28 | 4.28 | |

TABLE 2-21

(Composition 771-3)

| INGREDIENT | WT (g) | WT % | % ACTIVE |
|---|---|---|---|
| DGA dicamba (CLARITY ®) | 64.11 | 64.11 | 25.32 |
| potassium hydroxide | 18.82 | 18.82 | |

TABLE 2-21-continued (Composition 771-3)

| INGREDIENT | WT (g) | WT % | % ACTIVE |
|---|---|---|---|
| acetic acid | 13.52 | 13.52 | |
| water | 3.55 | 3.55 | |

TABLE 2-22

(Composition 871-2)

| INGREDIENT | WT (g) | WT % | % ACTIVE |
|---|---|---|---|
| DGA dicamba (CLARITY ®) | 73.43 | 73.43 | 29.00 |
| potassium hydroxide | 9.50 | 9.50 | |
| acetic acid | 5.91 | 5.91 | |
| PF 8000 Surfactant | 1.00 | 1.00 | |
| water | 10.16 | 10.16 | |

TABLE 2-23

(Composition 871-3)

| INGREDIENT | WT (g) | WT % | % ACTIVE |
|---|---|---|---|
| DGA dicamba (CLARITY ®) | 73.07 | 73.07 | 28.86 |
| potassium hydroxide | 11.00 | 11.00 | |
| acetic acid | 5.88 | 5.88 | |
| PF 8000 Surfactant | 1.00 | 1.00 | |
| water | 9.05 | 9.05 | |

TABLE 2-24

(Composition 871-6)

| INGREDIENT | WT (g) | WT % | % ACTIVE |
|---|---|---|---|
| DGA dicamba (CLARITY ®) | 73.07 | 73.07 | 28.86 |
| potassium hydroxide | 5.88 | 5.88 | |
| acetic acid | 11.00 | 11.00 | |
| water | 10.05 | 10.05 | |

Example 2-D: Liquid Concentrate Compositions (Dicamba+Glyphosate)

TABLE 2-24

(Composition 540-1)

| INGREDIENT | WT (g) | WT % | % ACTIVE |
|---|---|---|---|
| CLARITY ® (39.4% ae) | 24.87 | 24.87 | 9.8 |
| 1.35 MEA glyphosate (45.6% ae) | 42.98 | 42.98 | 19.6 |
| Ethoquad C12 75 DEG | 3.5 | 3.5 | |
| SAG 1572 | 0.01 | 0.01 | |
| Ferric sulfate | 0.14 | 0.14 | |
| Citric Acid | 0.26 | 0.26 | |
| Acetic acid | 5.32 | 5.32 | |
| potassium hydroxide (45% solution) | 7.33 | 7.33 | |
| water | 15.59 | 15.59 | |

TABLE 2-25

(Composition 085-1)

| INGREDIENT | WT (g) | WT % | % ACTIVE |
|---|---|---|---|
| CLARITY ® (39.4% ae) | 24.87 | 24.87 | 9.8 |
| 1.35 MEA glyphosate (45.6% ae) | 42.98 | 42.98 | 19.6 |
| Ethoquad C12 75 DEG | 3.5 | 3.5 | |
| SAG 1572 | 0.01 | 0.01 | |
| Ferric sulfate | 0.14 | 0.14 | |
| Citric acid | 0.26 | 0.26 | |
| acetic acid | 5.32 | 5.32 | |
| potassium hydroxide | 11.11 | 11.11 | |
| water | 11.81 | 11.81 | |

TABLE 2-26

(Composition 261)

| INGREDIENT | T (g) | WT % | % ACTIVE |
|---|---|---|---|
| CLARITY ® (39.4% ae) | 24.87 | 24.87 | 9.8 |
| 1.35 MEA glyphosate (45.6% ae) | 42.98 | 42.98 | 19.6 |
| AGM 550 | 2.5 | 2.5 | |
| Agnique PG 8107-G | 2.0 | 2.0 | |
| SAG 1572 | 0.01 | 0.01 | |
| Ferric sulfate | 0.14 | 0.14 | |
| Citric Acid | 0.26 | 0.26 | |
| Acetic acid | 5.32 | 5.32 | |
| potassium hydroxide (45% soln) | 7.33 | 7.33 | |
| water | 14.59 | 14.59 | |

TABLE 2-27

(Composition 567-2)

| INGREDIENT | WT (g) | WT % | % ACTIVE |
|---|---|---|---|
| CLARITY ® (39.4% ae) | 26.02 | 26.02 | 10.25 |
| 1.35 MEA glyphosate (45.6% ae) | 44.96 | 44.96 | 20.5 |
| AGM 550 | 2.5 | 2.5 | |
| Agnique PG 8107-G | 2.2 | 2.2 | |
| SAG 1572 | 0.01 | 0.01 | |
| Ferric sulfate | 0.14 | 0.14 | |
| Citric Acid | 0.26 | 0.26 | |
| Acetic acid | 5.57 | 5.57 | |
| potassium hydroxide (45% soln) | 7.67 | 7.67 | |
| water | 10.67 | 10.67 | |

TABLE 2-28

(Composition 331-3)

| INGREDIENT | WT (g) | WT % | % ACTIVE |
|---|---|---|---|
| CLARITY ® (39.4% ae) | 24.87 | 24.87 | 9.8 |
| 1.35 MEA glyphosate (45.6% ae) | 42.98 | 42.98 | 19.6 |
| AGM 550 | 2.5 | 2.5 | |
| Agnique PG 8107-G | 2.0 | 2.0 | |
| SAG 1572 | 0.01 | 0.01 | |
| Ferric sulfate | 0.14 | 0.14 | |
| Citric Acid | 0.26 | 0.26 | |
| Acetic acid | 5.32 | 5.32 | |
| potassium hydroxide (45% soln) | 11.11 | 11.11 | |
| water | 10.81 | 10.81 | |

TABLE 2-29

(Composition 249-3)

| INGREDIENT | WT (g) | WT % | % ACTIVE |
|---|---|---|---|
| DGA dicamba (55.2% ae) | | 17.93 | 9.90 |
| 1.35 MEA glyphosate (46.8% ae) | | 42.31 | 19.80 |
| AGM 550 | | 2.50 | |
| Agnique PG 8107-G | 2.0 | 2.0 | |
| SAG 1572 | 0.01 | 0.01 | |
| Ferric sulfate | 0.19 | 0.19 | |
| Citric Acid | 0.30 | 0.30 | |
| Potassium acetate (38.7% AcOH) | 13.95 | 13.95 | 5.40 |
| water | 20.81 | 20.81 | |

Example 2-E: Dry Concentrate Compositions (Dicamba)

Dry granules having the compositions shown in Table 2-30 and Table 2-31 were prepared. The sodium dicamba and the sodium acetate were mixed together in a blender. The PEG 8000, antifoam, and water were then added to the blender and mixing continued. The amount of water added was an amount sufficient to generate a paste suitable for extrusion. The paste was extruded under pressure through a 1 mm opening to obtain granules. The granules were extruded a total of three times to obtain granules that were not too dry. The final extruded granules were then dried in a fluidized bed dryer at 70° C. to yield dry granules having an off-white color.

TABLE 2-30

(Composition T2-30)

| INGREDIENT | WT (g) | WT % | % ACTIVE |
|---|---|---|---|
| Sodium dicamba | 85.00 | 85.00 | 68.0 |
| Sodium acetate | 10.00 | 10.00 | |
| PEG 8000 | 4.90 | 4.90 | |
| Antifoam (Momentive, SAG 1572) | 0.10 | 0.10 | |

TABLE 2-31

(Composition T2-31)

| INGREDIENT | WT (g) | WT % | % ACTIVE |
|---|---|---|---|
| Sodium dicamba | 81.25 | 81.25 | 65.0 |
| Sodium acetate | 10.00 | 10.00 | |
| PEG 8000 | 4.90 | 4.90 | |
| Antifoam (Momentive, SAG 1572) | 0.10 | 0.10 | |

Example 3: Measurement of Dicamba Volatility (Humidome)

Humidomes obtained from Hummert International (Part Nos 14-3850-2 for humidomes and 11-3050-1 for 1020 flat tray) were modified by cutting a 2.2 cm diameter hole on one end approximately 5 cm from the top to allow for insertion of a glass air sampling tube (22 mm OD) containing a polyurethane foam (PUF) filter. The sampling tube was secured with a VITON o-ring on each side of the humidome wall. The air sampling tube external to the humidome was fitted with tubing that was connected to a vacuum manifold immediately prior to sampling.

The flat tray beneath the humidome was filled with 1 liter of sifted dry or wet 50/50 soil (50% Redi-Earth and 50% US 10 Field Soil) to a depth of about 1 cm. The flat tray bottom containing the dicamba formulation on soil was covered with the humidome lid and the lid was secured with clamps. The assembled humidomes were placed in a temperature and humidity controlled environment and connected to a vacuum manifold through the air sampling line. Air was drawn through the humidome and PUF at a rate of 2 liters per minute (LPM) for 24 hours at which point the air sampling was stopped. The humidomes were then removed from the controlled environment and the PUF filter was removed. The PUF filter was extracted with 20 mL of methanol and the solution was analyzed for dicamba concentration using LC-MS methods known in the art.

To measure the dicamba concentration in the gas phase (air) that volatilized from the spray solutions, compositions were prepared to contain 1.2% a.e. dicamba which is equivalent to an application rate of 1.0 lb/A a.e. at 10 gallons per acre (GPA). Where glyphosate was added or was part of the formulation, glyphosate was present at a concentration of 2.4% a.e. or 2.0 lb/A a.e. Where 2,4-D was added or was part of the formulation, 2,4-D was present at 2.4% ae or 2.0 lb/A ae at 10 gallons per acre (GPA). The growth chambers were set at 35° C. and 40% relative humidity (RH). For each composition four separate humidome boxes were sprayed to have 4 replicate measurements for each formulation. Tables 3-1 to 3-12 below provide the mean concentration of dicamba in air for the tested formulations. Where concentrations of dicamba were below the limits of detection, "nd" is indicated in the tables below.

Humidome Results:

TABLE 3-1

| ID | COMPOSITION | DICAMBA (ng/L) | STD DEV | STD ERROR |
|---|---|---|---|---|
| 854-A | 1.2% ae CLARITY ® | 0.03 | 0.00 | 0.00 |
| 854-B | 1.2% ae CLARITY ® + 2.4% ae POWERMAX ® | 0.44 | 0.11 | 0.06 |
| 854-F | 1.2% ae CLARITY ® + 2.4% ae POWERMAX ® + 2% potassium acetate | nd | na | na |
| 854-C | 1.2% ae CLARITY ® + 2.4% ae POWERMAX ® + 2% dipotassium phosphate | 0.06 | 0.01 | 0.01 |
| 854-D | 1.2% ae CLARITY ® 2.4% ae POWERMAX ® + 2% potassium oxalate | 0.47 | 0.13 | 0.06 |
| 854-E | 1.2% ae CLARITY ® 2.4% ae POWERMAX ® + 2% potassium citrate | 0.33 | 0.20 | 0.10 |

TABLE 3-2

| ID | COMPOSITION | DICAMBA (ng/L) | STD DEV | STD ERROR |
|---|---|---|---|---|
| 854-A | 1.2% ae CLARITY ® | 0.02 | 0.00 | 0.00 |
| 854-B | 1.2% ae CLARITY ® + 2.4% ae POWERMAX ® | 0.49 | 0.16 | 0.08 |

TABLE 3-2-continued

| ID | COMPOSITION | DICAMBA (ng/L) | STD DEV | STD ERROR |
|---|---|---|---|---|
| 731-C | 1.2% ae CLARITY ® + 2.4% ae POWERMAX ® + 2% potassium acetate | nd | na | na |
| 854-C | 1.2% ae CLARITY ® + 2.4% ae POWERMAX ® + 2% dipotassium phosphate | 0.04 | 0.01 | 0.01 |

TABLE 3-3

| ID | COMPOSITION | DICAMBA (ng/L) | STD DEV | STD ERROR |
|---|---|---|---|---|
| 751-A | 1.2% ae CLARITY ® | 0.02 | 0.00 | 0.00 |
| 751-B | 1.2% ae CLARITY ® + 2.4% ae POWERMAX ® | 1.04 | 0.50 | 0.25 |
| 751-E | 1.2% ae CLARITY ® + 2.4% ae POWERMAX ® + 1% AMS | 6.13 | 0.55 | 0.32 |
| 751-C | 1.2% ae CLARITY ® + 2.4% ae PowerMAX + 2% potassium acetate | nd | na | na |
| 751-D | 1.2% ae CLARITY ® + 2.4% ae POWERMAX ® + 2% potassium acetate + 1% ammonium sulfate | 3.63 | 0.77 | 0.38 |

TABLE 3-4

| ID | COMPOSITION | DICAMBA (ng/L) | STD DEV | STD ERROR |
|---|---|---|---|---|
| 210-A | 1.2% ae CLARITY ® + 2.4% ae POWERMAX ® | 0.92 | 0.22 | 0.11 |
| 210-B | 1.2% ae Clarity + 2.4% ae POWERMAX ® + 2% potassium acetate | nd | na | na |
| 210-C | 1.2% ae CLARITY ® + 2.4% ae POWERMAX ® + 2% potassium acetate + 1% ammonium sulfate | 0.16 | 0.02 | 0.01 |
| 210-D | 1.2% ae CLARITY ® + 2.4% ae POWERMAX ® + 2% potassium acetate/ dipotassium phosphate | 0.01 | 0.00 | 0.00 |

TABLE 3-5

| ID | COMPOSITION | DICAMBA (ng/L) | STD DEV | STD ERROR |
|---|---|---|---|---|
| 870-A | 2.4% ae DURANGO ® DMA ® + 2.4% 2,4-D amine | 0.10 | 0.03 | 0.01 |
| 870-B | 2.4% ae DURANGO ® DMA ® + 2.4% 2,4-D amine + 2% potassium acetate | 0.01 | 0.00 | 0.00 |
| 870-D | 2.4% ae IPA glyphosate + 2.4% ae 2,4-D amine | 0.09 | 0.03 | 0.01 |
| 870-C | 2.4% ae IPA glyphosate + 2.4% ae 2,4-D amine + 2% potassium acetate | 0.01 | 0.01 | 0.00 |

TABLE 3-6

| ID | COMPOSITION | DICAMBA (ng/L) | STD DEV | STD ERROR |
|---|---|---|---|---|
| 563-2 | 1.2% ae BANVEL ® + 2.4% POWERMAX ® | 1.92 | 0.31 | 0.15 |

TABLE 3-6-continued

| ID | COMPOSITION | DICAMBA (ng/L) | STD DEV | STD ERROR |
|---|---|---|---|---|
| 563-5 | 1.2% ae BANVEL ® + 2.4% POWERMAX ® + 2% potassium acetate | 0.02 | 0.01 | 0.00 |
| 563-3 | 1.2% ae CLARITY ® + 2.4% ae PowerMAX | 0.49 | 0.13 | 0.06 |
| 563-6 | 1.2% ae CLARITY ® + 2.4% ae POWERMAX ® + 2% potassium acetate | 0.01 | 0.01 | 0.00 |
| 563-1 | 1.2% ae MEA dicamba + 2.4% ae POWERMAX ® | 1.04 | 0.24 | 0.12 |
| 563-4 | 1.2% ae MEA dicamba + 2.4% ae POWERMAX ® + 2% potassium acetate | 0.01 | 0.00 | 0.00 |

TABLE 3-7

| ID | COMPOSITION | DICAMBA (ng/L) | STD DEV | STD ERROR |
|---|---|---|---|---|
| 751-F | 1.2% ae DGA dicamba/MEA glyphosate premix + 2% potassium acetate | nd | na | na |
| 210-E | 1.2% ae DGA dicamba/MEA glyphosate/ 0.54% potassium acetate premix | 0.07 | 0.01 | 0.00 |
| 210-F | 1.2% DGA dicamba/MEA glyphosate premix + 2% potassium acetate/dipotassium phosphate | 0.01 | 0.00 | 0.00 |

TABLE 3-8

| ID | COMPOSITION | DICAMBA (ng/L) | STD DEV | STD ERROR |
|---|---|---|---|---|
| 893-A | 1.2% ae CLARITY ® + 2.4% POWERMAX ® | 0.83 | 0.10 | 0.05 |
| 893-B | 1.2% ae CLARITY ® + 2.4% POWERMAX ® + 2% potassium acetate | 0.003 | 0.00 | 0.00 |
| 893-C | 1.2% ae CLARITY ® + 2.4% POWERMAX ® + 2% potassium benzoate | 0.007 | 0.00 | 0.00 |
| 893-D | 1.2% ae CLARITY ® + 2.4% POWERMAX ® + 2% potassium formate | 0.003 | 0.00 | 0.00 |
| 893-E | 1.2% ae CLARITY ® + 2.4% POWERMAX ® + 2% sodium acetate | 0.001 | 0.00 | 0.00 |

TABLE 3-9

| ID | COMPOSITION | MOLAR RATIO CARBOXYLIC ACID:DICAMBA | MOLAR RATIO CARBOXYLIC ACID:KOH | DICAMBA (ng/L) | STD DEV | STD ERR |
|---|---|---|---|---|---|---|
| 836-1 | 1.2% ae CLARITY ® + 2.4% POWERMAX ® | NA | NA | 1.139 | 0.34 | 0.17 |
| 836-6 | 1.2% ae CLARITY ® + 2.4% POWERMAX ® + potassium hydroxide | NA | NA | 0.029 | 0.01 | 0.00 |
| 836-3 | 1.2% ae CLARITY ® + 2.4% POWERMAX ® + propionic acid + potassium hydroxide | 2:1 | 1:1 | 0.011 | 0.01 | 0.00 |
| 836-5 | 1.2% ae CLARITY ® + 2.4% POWERMAX ® + formic acid + potassium hydroxide | 2:1 | 1:1 | 0.012 | 0.00 | 0.00 |
| 836-2 | 1.2% ae CLARITY ® + 2.4% POWERMAX ® + succinic acid + potassium hydroxide | 2:1 | 1:2 | 0.064 | 0.01 | 0.01 |
| 836-4 | 1.2% ae CLARITY ® + 2.4% POWERMAX ® + acetic acid + potassium hydroxide | 2:1 | 1:1 | 0.014 | 0.01 | 0.00 |

TABLE 3-10

| ID | COMPOSITION* | DICAMBA (ng/L) | STD DEV | STD ERROR |
|---|---|---|---|---|
| 321-1 | 1.2% ae CLARITY ® | 0.016 | 0.005 | 0.003 |
| 321-2 | 1.2% Composition 871-2 | 0.004 | 0.001 | 0.001 |
| 321-3 | 1.2% Composition 871-3 | 0.005 | 0.003 | 0.002 |
| 321-4 | 1.2% Composition 871-4 | 0.003 | 0.000 | 0.000 |
| 321-5 | 1.2% Composition 871-5 | 0.003 | 0.000 | 0.000 |
| 321-6 | 1.2% Composition 871-6 | 0.003 | 0.001 | 0.000 |

*Test formulation was prepared by diluting referenced Composition with an amount of water sufficient to provide a test formulation containing 1.2% a.e. dicamba.

TABLE 3-11

| ID | COMPOSITION* | DICAMBA (ng/L) | STD DEV | STD ERROR |
|---|---|---|---|---|
| 891-1 | 1.2% ae CLARITY ® | 0.367 | 0.110 | 0.039 |
| 917-2 | 1.2% ae CLARITY ® + 2.4% ae POWERMAX ® | 0.015 | 0.004 | 0.001 |
| 917-3 | 1.2% ae Composition 261 | 0.006 | 0.002 | 0.000 |

*Test formulation was prepared by diluting referenced Composition with an amount of water sufficient to provide a test formulation containing 1.2% a.e. dicamba.

TABLE 3-12

| ID | COMPOSITION* | DICAMBA (ng/L) | STD DEV | STD ERROR |
|---|---|---|---|---|
| 364-1 | 1.2% ae CLARITY ® | 0.049 | 0.018 | 0.009 |
| 364-2 | 1.2% ae Clarity + 3.36% v/v Liberty | 1.938 | 0.020 | 0.012 |
| 364-3 | 1.2% ae Clarity + 3.36% v/v Liberty + 3% v/v dipotassium phosphate | 0.031 | 0.013 | 0.007 |
| 364-4 | 1.2% ae Composition 871-5 | 0.002 | 0.003 | 0.001 |
| 364-5 | 1.2% ae Composition 871-5 + 3.36% v/v Liberty | 0.191 | 0.033 | 0.019 |
| 364-6 | 1.2% ae Composition 871-5 + 3.36% v/v Liberty + 3% dipotassium phosphate | 0.013 | 0.002 | 0.001 |

*Test formulation was prepared by diluting referenced Composition with an amount of water sufficient to provide a test formulation containing 1.2% a.e. dicamba.

TABLE 3-12

| ID | COMPOSITION* | DICAMBA (ng/L) | STD DEV | STD ERROR |
|---|---|---|---|---|
| 268-1 | 1.2% ae CLARITY ® + 2.4% ae ROUNDUP ® ENERGY | 4.76 | 0.96 | 0.48 |
| 268-2 | 1.2% ae CLARITY ® + 2.4% ae ROUNDUP ® ENERGY + 3% dipotassium phosphsate | 1.11 | 0.47 | 0.23 |
| 268-3 | 1.2% ae CLARITY ® + 2.4% ae ROUNDUP ® ENERGY + 2% potassium acetate | 0.17 | 0.13 | 0.06 |
| 268-4 | 1.2% ae CLARITY ® + 2.4% ae ROUNDUP ® ENERGY + 4% potassium acetate | 0.00 | 0.00 | 0.00 |
| 268-5 | 1.2% ae CLARITY ® + 2.4% ae ROUNDUP ® ENERGY + 2% potassium acetate + 3% dipotassium phosphate | 0.01 | 0.01 | 0.00 |
| 268-6 | 1.2% ae CLARITY + 2.4% ae PowerMAX | 1.55 | 0.52 | 0.26 |

*ROUNDUP ® ENERGY is the glyphosate ammonium salt, sold as water soluble granules in Europe.

The results reported above for the di- and tri-carboxylic acids tested (oxalic acid, citric acid, and succinic acid) indicate that those acids did not reduce dicamba volatility. In addition, malic acid was tested and likewise did not reduce dicamba volatility.

Example 4: Measurement of Dicamba Volatility (Plant Response)

Herbicidal compositions were sprayed onto eight 90 mm diameter glass Petri dishes. The eight Petri dishes were placed immediately on a plastic tray along with two Roundup Ready soybean plants at V1-V1.5 development stage as indicators. The plastic trays were then covered with plastic domes, sealed with clamps around edges, and placed in the growth chamber, at a set temperature and relative humidity (85° F. day (16 h light), 70° F. night (8 h dark) and 40% RH) for 24 hours. After 24 hours, the plants were removed from the domes and transferred to a greenhouse. The indicator plants were evaluated for visual symptoms typically at 5, 7 and 14 days after treatment.

Plant response results for compositions containing dicamba are listed in Tables 4-1, 4-2, and 4-3:

TABLE 4-1

| ID | COMPOSITION | % INJURY (7 DAT) |
|---|---|---|
| 889-A | 1.2% ae DGA dicamba | 15% |
| 889-D | 1.2% ae DGA dicamba + 2% potassium acetate | 0 |

TABLE 4-2

| ID | COMPOSITION* | % INJURY (7 DAT) | % INJURY (14 DAT) |
|---|---|---|---|
| 321-1 | 1.2% ae CLARITY ® | 10.00 | 23.33 |
| 321-2 | 1.2% Composition 871-2 | 0.00 | 5.13 |
| 321-3 | 1.2% Composition 871-3 | 0.63 | 8.50 |
| 321-4 | 1.2% Composition 871-4 | 4.13 | 15.38 |
| 321-5 | 1.2% Composition 871-5 | 2.63 | 10.75 |
| 321-6 | 1.2% Composition 871-6 | 5.38 | 15.38 |

*Test formulation was prepared by diluting referenced Composition with an amount of water sufficient to provide a test formulation containing 1.2% a.e. dicamba.

TABLE 4-3

| ID | COMPOSITION* | % INJURY (7 DAT) | % INJURY (14 DAT) |
|---|---|---|---|
| 891-1 | 1.2% ae CLARITY ® | 6.44 | 25.31 |
| 917-2 | 1.2% ae CLARITY ® + 2.4% ae POWERMAX ® | 12.50 | 44.38 |
| 917-3 | 1.2% ae Composition 261 | 3.25 | 9.75 |

*Test formulation was prepared by diluting referenced Composition with an amount of water sufficient to provide a test formulation containing 1.2% a.e. dicamba.

Example 5: Measurement of Herbicidal Effectiveness

The herbicidal effectiveness of the compositions of the present invention can be assessed through conventional greenhouse tests and/or field tests. Herbicidal effectiveness can be measured as a percentage "inhibition" following a standard procedure in the art which reflects a visual assessment of plant mortality and growth reduction by comparison with untreated plants, made by technicians specially trained to make and record such observations. In all cases, a single technician makes all assessments of percent inhibition within any one experiment or trial. Such measurements are relied upon and regularly reported by Monsanto Technology LLC in the course of its herbicide business.

The selection of application rates that are biologically effective for a specific auxin herbicide is within the skill of the ordinary agricultural scientist. Those of skill in the art will likewise recognize that individual plant conditions, weather and growing conditions, as well as the specific exogenous chemical and formulation thereof selected, will affect the weed efficacy and associated crop injury achieved in practicing this invention. Useful application rates for the auxin herbicides employed can depend upon all of the above conditions. With respect to the use of the method of this invention, much information is known about appropriate auxin application rates, and a weed control practitioner can select auxin application rates that are herbicidally effective on particular species at particular growth stages in particular environmental conditions.

Effectiveness in greenhouse tests, usually at exogenous chemical rates lower than those normally effective in the field, is a proven indicator of consistency of field performance at normal use rates.

The compositions of the present invention can be applied to plants by spraying, using any conventional means for spraying liquids, such as spray nozzles, atomizers, or the like. Compositions of the present invention can be used in precision farming techniques, in which apparatus is employed to vary the amount of exogenous chemical applied to different parts of a field, depending on variables such as the particular plant species present, soil composition, and the like. In one embodiment of such techniques, a global positioning system operated with the spraying apparatus can be used to apply the desired amount of the composition to different parts of a field.

The composition, at the time of application to plants, is preferably dilute enough to be readily sprayed using standard agricultural spray equipment. Preferred application rates for the present invention vary depending upon a number of factors, including the type and concentration of active ingredient and the plant species involved. Useful rates for applying an aqueous composition to a field of foliage can range from about 25 to about 1,000 liters per hectare (1/ha) by spray application. The preferred application rates for aqueous solutions are in the range from about 50 to about 300 l/ha.

Many exogenous chemicals (including auxin herbicides) must be taken up by living tissues of the plant and translocated within the plant in order to produce the desired biological (e.g., herbicidal) effect. Thus, it is important that an herbicidal formulation not be applied in such a manner as to excessively injure and interrupt the normal functioning of the local tissue of the plant so quickly that translocation is reduced. However, some limited degree of local injury can be insignificant, or even beneficial, in its impact on the biological effectiveness of certain exogenous chemicals.

Results obtained with application of the composition to green foxtail (SETVI), velvetleaf (ABUTH), and hemp sesbania (SEBEX) are shown in Tables 5-1, 5-2, and 5-3, respectively. In each case, application rates were 280 g ae/ha for dicamba and 560 g ae/ha for glyphosate, and the reported result is an average of the results obtained from six separate applications.

TABLE 5-2

Green Foxtail (SETVI)

| Composition | AVG % CONTROL |
|---|---|
| ROUNDUP POWERMAX ® + CLARITY ® | 99.7 |
| Composition 249-3 | 99.7 |

TABLE 5-2

Velvetleaf (ABUTH)

| Composition | AVG % CONTROL |
|---|---|
| ROUNDUP POWERMAX ® + CLARITY ® | 90.8 |
| Composition 249-3 | 86.7 |

TABLE 5-2

Hemp *Sesbania* (SEBEX)

| Composition | AVG % CONTROL |
|---|---|
| ROUNDUP POWERMAX ® + CLARITY ® | 99.2 |
| Composition 249-3 | 100 |

Example 6: Herbicidal Efficacy on ABUTH (Velvetleaf) and ELEIN (Gooseqrass)

The herbicidal tank mix compositions listed in the tables below were prepared using CLARITY® (DGA dicamba from BASF) and ROUNDUP POWERMAX® (potassium glyphosate from Monsanto) by successively adding each specified herbicide to water and mixing. The tank mixtures containing potassium acetate were prepared as described in Example 1.

Weed seeds were planted in 3.5 in square plastic pots filled with Redi-earth (Sun Gro, Bellevue, Wash.) containing 100 g/cu ft Osmocote 14-14-14 slow release fertilizer. Ten to fifteen weed seeds were planted about one-half inch deep and loosely covered with Redi-Earth potting media. The pots were placed in a controlled environment equipped with sub-irrigation. Growth conditions were 27° C. day and 21° C. night with fourteen hours of supplemental light (approximately 600 microeinsteins). After germination and emergence from the potting media, the plants were thinned to achieve one plant per pot. Pots that contained plants that were similar in appearance, size, and vigor were selected for treatment. Typically, the plants were four to eight inches tall at the time of herbicide treatment. Compositions were applied to the plants with a track sprayer generally using a Teejet 9501E flat fan nozzle or similar nozzle with air pressure set at a minimum of 24 pounds per square inch. The spray nozzle was 16 inches above the top of the plants and a spray volume rate of approximately 10 gallons per acre (93 L per hectare) was applied. Each composition was applied at three application rates and herbicide injury rating was made 21 days post treatment.

TABLE 6-1

Herbicidal Efficacy of Tank Mixtures Containing POWERMAX ® and DGA dicamba/potassium acetate on ABUTH (velvetleaf) and ELEIN (goosegrass)

| COMPOSITION | AMT (% ae) | RATE | % CONTROL (21 DAT) ABUTH | ELEIN |
|---|---|---|---|---|
| POWERMAX ® | 39.8 | 140 ae g/ha | 0.0 | 23.3 |
|  |  | 280 ae g/ha | 52.5 | 85.0 |
|  |  | 560 ae g/ha | 74.2 | 93.8 |
| CLARITY ® | 40 | 70 ae g/ha | 10.0 | 0.0 |
|  |  | 140 ae g/ha | 18.3 | 10.0 |
|  |  | 280 ae g/ha | 36.7 | 10.0 |
| 503-1 | 31.0 | 70 ae g/ha | 10.8 | 0.0 |
| 503-1 | 31.0 | 140 ae g/ha | 19.2 | 0.0 |
| 503-1 | 31.0 | 280 ae g/ha | 33.3 | 0.0 |
| 503-3 | 31.0 | 70 ae g/ha | 10.0 | 8.3 |
| 503-3 | 31.0 | 140 ae g/ha | 17.5 | 11.7 |
| 503-3 | 31.0 | 280 ae g/ha | 35.0 | 7.5 |
| 295-3 | 31.0 | 70 ae g/ha | 13.3 | 8.3 |
| 295-3 | 31.0 | 140 ae g/ha | 20.0 | 11.7 |
| 295-3 | 31.0 | 280 ae g/ha | 36.7 | 7.5 |
| 295-6 | 31.0 | 70 ae g/ha | 12.5 | 0.0 |
| 295-6 | 31.0 | 140 ae g/ha | 21.7 | 0.0 |
| 295-6 | 31.0 | 280 ae g/ha | 43.3 | 3.3 |
| POWERMAX ® CLARITY ® | 39.8 40 | 140 ae g/ha 70 ae g/ha | 14.2 | 38.3 |
| POWERMAX ® CLARITY ® | 39.8 40 | 280 ae g/ha 140 ae g/ha | 46.7 | 85.0 |
| POWERMAX ® CLARITY ® | 39.8% ae 40% ae | 560 ae g/ha 280 ae g/ha | 80.8 | 95.0 |
| POWERMAX ® 503-1 | 39.8% ae 31.0% ae | 140 ae g/ha 70 ae g/ha | 11.7 | 39.2 |
| POWERMAX ® 503-1 | 39.8% ae 31.0% ae | 280 ae g/ha 140 ae g/ha | 62.5 | 81.7 |
| POWERMAX ® 503-1 | 39.8% ae 31.0% ae | 560 ae g/ha 280 ae g/ha | 82.5 | 94.2 |

TABLE 6-1-continued

Herbicidal Efficacy of Tank Mixtures Containing POWERMAX ® and DGA dicamba/potassium acetate on ABUTH (velvetleaf) and ELEIN (goosegrass)

| COMPOSITION | AMT (% ae) | RATE | % CONTROL (21 DAT) ABUTH | ELEIN |
|---|---|---|---|---|
| POWERMAX ® 503-3 | 39.8% ae 31.0% ae | 140 ae g/ha 70 ae g/ha | 15.0 | 35.0 |
| POWERMAX ® 503-3 | 39.8% ae 31.0% ae | 280 ae g/ha 140 ae g/ha | 49.2 | 83.3 |
| POWERMAX ® 503-3 | 39.8% ae 31.0% ae | 560 ae g/ha 280 ae g/ha | 83.3 | 93.3 |
| POWERMAX ® 295-3 | 39.8% ae 31.0% ae | 140 ae g/ha 70 ae g/ha | 15.8 | 26.7 |
| POWERMAX ® 295-3 | 39.8% ae 31.0% ae | 280 ae g/ha 140 ae g/ha | 54.2 | 82.5 |
| POWERMAX ® 295-3 | 39.8% ae 31.0% ae | 560 ae g/ha 280 ae g/ha | 83.3 | 90.0 |
| POWERMAX ® 295-6 | 39.8% ae 31.0% ae | 140 ae g/ha 70 ae g/ha | 17.5 | 42.5 |
| POWERMAX ® 295-6 | 39.8% ae 31.0% ae | 280 ae g/ha 140 ae g/ha | 55.0 | 80.0 |
| POWERMAX ® 295-6 | 39.8% ae 31.0% ae | 560 ae g/ha 280 ae g/ha | 85.8 | 85.0 |
| UNTREATED CHECK | 0 | 0 | 0.0 | 1.0 |

Herbicidal premix compositions listed in the tables below were prepared as previously described in Example 2.

TABLE 6-2

Herbicidal efficacy of premix composition containing glyphosate, dicamba and potassium acetate on ABUTH (velvetleaf) and ELEIN (goosegrass)

| COMPOSITION | RATE | % CONTROL (21 DAT) ABUTH | ELEIN |
|---|---|---|---|
| POWERMAX ® | 140 ae g/ha | 21.7 | 78.3 |
|  | 280 ae g/ha | 71.7 | 95.0 |
|  | 560 ae g/ha | 84.2 | 99.0 |
| CLARITY ® | 70 ae g/ha | 20.0 | 0.0 |
|  | 140 ae g/ha | 36.7 | 0.0 |
|  | 280 ae g/ha | 60.8 | 0.0 |
| POWERMAX ® CLARITY ® | 140 ae g/ha 70 ae g/ha | 26.7 | 81.7 |
| POWERMAX ® CLARITY ® | 280 ae g/ha 140 ae g/ha | 59.2 | 90.0 |
| POWERMAX ® CLARITY ® | 560 ae g/ha 280 ae g/ha | 85.8 | 92.5 |
| RATE GLY/DICAMBA | | | |
| 287-5 | 140/70 ae g/ha | 20.0 | 0.0 |
|  | 280/140 ae g/ha | 51.7 | 10.0 |
|  | 560/280 ae g/ha | 71.7 | 68.3 |
| 287-6 | 140/70 ae g/ha | 18.3 | 0.0 |
|  | 280/140 ae g/ha | 50.0 | 10.0 |
|  | 560/280 ae g/ha | 73.3 | 39.2 |
| 512-1 | 140/70 ae g/ha | 22.5 | 84.2 |
|  | 280/140 ae g/ha | 64.2 | 93.3 |
|  | 560/280 ae g/ha | 92.7 | 97.2 |
| 248-1 | 140/70 ae g/ha | 32.5 | 78.3 |
|  | 280/140 ae g/ha | 63.3 | 92.2 |
|  | 560/280 ae g/ha | 85.5 | 95.0 |
| 248-2 | 140/70 ae g/ha | 38.3 | 78.3 |
|  | 280/140 ae g/ha | 57.5 | 93.3 |
|  | 560/280 ae g/ha | 85.8 | 95.0 |
| 248-3 | 140/70 ae g/ha | 30.0 | 80.8 |
|  | 280/140 ae g/ha | 51.7 | 90.8 |
|  | 560/280 ae g/ha | 84.7 | 96.5 |

TABLE 6-2-continued

Herbicidal efficacy of premix composition containing glyphosate, dicamba and potassium acetate on ABUTH (velvetleaf) and ELEIN (goosegrass)

| COMPOSITION | | % CONTROL (21 DAT) ABUTH | ELEIN |
|---|---|---|---|
| 249-1 | 140/70 ae g/ha | 33.3 | 81.7 |
|  | 280/140 ae g/ha | 59.2 | 90.0 |
|  | 560/280 ae g/ha | 92.2 | 98.0 |
| 249-2 | 140/70 ae g/ha | 30.0 | 80.8 |
|  | 280/140 ae g/ha | 58.3 | 90.8 |
|  | 560/280 ae g/ha | 89.7 | 97.3 |
| 249-3 | 140/70 ae g/ha | 30.8 | 86.7 |
|  | 280/140 ae g/ha | 63.3 | 91.7 |
|  | 560/280 ae g/ha | 86.7 | 98.2 |
| UNTREATED CHECK | 0 | 0.0 | 0.0 |

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A herbicidal composition concentrate comprising:
   dicamba, or an agriculturally acceptable salt or ester thereof; and
   a potassium or sodium monocarboxylate of a monocarboxylic acid;
   wherein:
      the concentrate comprises an amount of the potassium or sodium monocarboxylate sufficient to reduce the concentration of volatilized dicamba in the vapor phase surrounding a diluted version of the concentrate relative to the concentration of volatilized dicamba in the vapor phase surrounding an otherwise identical diluted version of the concentrate lacking the potassium or sodium monocarboxylate.

2. The herbicidal composition concentrate of claim 1, wherein the concentrate comprises an agriculturally acceptable salt of dicamba selected from the group consisting of N,N-bis-[aminopropyl]methylamine, monoethanolamine, dimethylamine, isopropylamine, diglycolamine, potassium, and sodium salts, and combinations thereof.

3. The herbicidal composition concentrate of claim 1, wherein the concentrate comprises the diglycolamine salt of dicamba.

4. The herbicidal composition concentrate of claim 1, wherein the monocarboxylic acid is selected from the group consisting of formic acid, acetic acid, propionic acid, and benzoic acid.

5. The herbicidal composition concentrate of claim 1, wherein the concentrate comprises the potassium or sodium monocarboxylate salt, in whole or in part, in dissociated form, the monocarboxylate salt selected from the group consisting of formate salts, acetate salts, propionate salts, and benzoate salts of the monocarboxylic acid.

6. The herbicidal composition concentrate of claim 1, wherein the concentrate comprises acetic acid, or an agriculturally acceptable salt thereof.

7. The herbicidal composition concentrate of claim 1, wherein the concentrate comprises an additive selected from the group consisting of surfactants, drift reduction agents, safeners, solubility enhancing agents, thickening agents, flow enhancers, foam-moderating agents, freeze protectants, UV protectants, preservatives, antimicrobials, and/or other additives that are necessary or desirable to improve the performance, crop safety, or handling of the composition.

8. The herbicidal composition concentrate of claim 1, wherein the concentrate comprises less than about 10 ppm of ammonium sulfate.

9. The herbicidal composition concentrate of claim 1, wherein the concentrate contains dicamba at a total loading of from about 120 to about 600 g acid equivalent (a.e.)/L.

10. The herbicidal composition concentrate of claim 1, wherein the concentrate contains dicamba at a total loading of from about 300 g a.e./L to about 600 g a.e./L.

11. The herbicidal composition concentrate of claim 1, wherein the concentrate contains dicamba at a total loading of from about 350 g a.e./L to about 600 g a.e./L.

12. The herbicidal composition concentrate of claim 1, wherein the concentrate contains dicamba at a total loading of from about 400 g a.e./L to about 600 g a.e./L.

13. The herbicidal composition concentrate of claim 1, wherein the concentrate contains dicamba at a total loading of from about 450 g a.e./L to about 600 g a.e./L.

14. The herbicidal composition concentrate of claim 1, wherein the concentrate contains dicamba at a total loading of from about 500 g a.e./L to about 600 g a.e./L.

15. The herbicidal composition concentrate of claim 1, wherein the composition is a liquid concentrate containing a total amount (acid equivalent weight) of dicamba from about 5% to about 75% by weight of the concentrate.

16. The herbicidal composition concentrate of claim 1, wherein the composition is a liquid concentrate containing a total amount (acid equivalent weight) of dicamba from about 25% to about 35% by weight of the concentrate.

17. The herbicidal composition concentrate of claim 1, wherein the composition is a dry concentrate containing a total amount (acid equivalent weight) of dicamba from about 40% to about 90% by weight of the concentrate.

18. The herbicidal composition concentrate of claim 1, wherein the molar ratio of dicamba to the potassium or sodium monocarboxylate, is from about 1:10 to about 10:1.

19. The herbicidal composition concentrate of claim 1, wherein the molar ratio of dicamba to the potassium or sodium monocarboxylate, is from about 2:1 to about 1:2.

20. The herbicidal composition concentrate of claim 1, wherein the concentration of the potassium or sodium monocarboxylate, is from about 1 gram (acid equivalent weight)/L to about 250 grams (acid equivalent weight)/L.

21. The herbicidal composition concentrate of claim 1, wherein the concentrate comprises an amount (acid equivalent weight) of the potassium or sodium monocarboxylate, of from about 1% to about 20% by weight of the concentrate.

22. The herbicidal composition concentrate of claim 1, wherein the concentrate comprises an amount (acid equivalent weight) of the potassium or sodium monocarboxylate, of from about 2% to about 15% by weight of the concentrate.

23. The herbicidal composition concentrate of claim 1, wherein the concentrate is a liquid concentrate and comprises an amount (acid equivalent weight) of the monocarboxylate, of from about 2% to about 10% by weight of the concentrate.

24. The herbicidal composition concentrate of claim 1, wherein the concentrate is a dry concentrate and comprises an amount (acid equivalent weight) of the monocarboxylate, of from about 5% to about 15% by weight of the concentrate.

25. The herbicidal composition concentrate of claim 1, wherein the composition comprises:
acetic acid, or an agriculturally acceptable salt thereof;
wherein the molar ratio of acetic acid, or agriculturally acceptable salt thereof, to dicamba, or agriculturally acceptable salt or ester thereof, is from about 1:10 to about 10:1; and/or
wherein the acid equivalent weight ratio of acetic acid, or agriculturally acceptable salt thereof, to dicamba, or agriculturally acceptable salt or ester thereof, is from about 1:10 to about 5:1; and/or
wherein the concentrate contains an amount (acid equivalent weight) of the acetic acid, or agriculturally acceptable salt thereof, from about 0.25% to about 25% by weight of the concentrate; and/or
wherein the concentration of the acetic acid, or agriculturally acceptable salt thereof, is from about 1 gram (acid equivalent weight)/L to about 250 grams (acid equivalent weight)/L; and/or
wherein the concentration of dicamba, or an agriculturally acceptable salt or ester thereof, is from about 120 grams (acid equivalent weight)/L to about 600 grams (acid equivalent weight)/L.

26. The herbicidal composition concentrate of claim 1, wherein the composition comprises:
acetic acid, or an agriculturally acceptable salt thereof;
wherein the concentration of dicamba, or an agriculturally acceptable salt or ester thereof, is from about 120 grams (acid equivalent weight)/L to about 600 grams (acid equivalent weight)/L; and
wherein the acid equivalent weight ratio of acetic acid, or agriculturally acceptable salt thereof, to dicamba, or agriculturally acceptable salt or ester thereof, is from about 1:10 to about 5:1.

27. The herbicidal composition concentrate of claim 1, wherein the composition comprises:
acetic acid, or an agriculturally acceptable salt thereof; and
wherein:
the concentrate contains an amount (acid equivalent weight) of the acetic acid, or agriculturally acceptable salt thereof, from about 1% to about 25% by weight of the concentrate; and
the concentrate contains an amount (acid equivalent weight) of dicamba, or an agriculturally acceptable salt or ester thereof, from about 10% to about 60% by weight of the concentrate.

28. The herbicidal composition concentrate of claim 1, wherein the composition comprises:
acetic acid, or an agriculturally acceptable salt thereof; and
wherein:
the concentrate contains an amount (acid equivalent weight) of the acetic acid, or agriculturally acceptable salt thereof, from about 2% to about 20% by weight of the concentrate; and
the concentrate contains an amount (acid equivalent weight) of dicamba, or an agriculturally acceptable salt or ester thereof, from about 15% to about 50% by weight of the concentrate.

29. The herbicidal composition concentrate of claim 1, wherein the composition comprises:

acetic acid, or an agriculturally acceptable salt thereof; and wherein:
the concentrate contains an amount (acid equivalent weight) of the acetic acid, or agriculturally acceptable salt thereof, from about 3% to about 15% by weight of the concentrate; and
the concentrate contains an amount (acid equivalent weight) of dicamba, or an agriculturally acceptable salt or ester thereof, from about 20% to about 40% by weight of the concentrate.

30. The herbicidal composition concentrate of claim 1, wherein the composition comprises:
acetic acid, or an agriculturally acceptable salt thereof; and
wherein:
the concentrate contains an amount (acid equivalent weight) of the acetic acid, or agriculturally acceptable salt thereof, from about 3% to about 10% by weight of the concentrate; and
the concentrate contains an amount (acid equivalent weight) of dicamba, or an agriculturally acceptable salt or ester thereof, from about 25% to about 35% by weight of the concentrate.

31. The herbicidal composition concentrate of claim 1, wherein the concentrate is a dry concentrate comprising:
acetic acid, or an agriculturally acceptable salt thereof; and
wherein:
the concentrate contains an amount (acid equivalent weight) of the acetic acid, or agriculturally acceptable salt thereof, from about 1% to about 40% by weight of the concentrate;
the concentrate contains an amount (acid equivalent weight) of dicamba, or an agriculturally acceptable salt or ester thereof, from about 40% to about 90% by weight of the concentrate; and
wherein the sum of the acetic acid weight percent and the dicamba weight percent is less than or equal to 100%.

32. The herbicidal composition concentrate of claim 1, wherein the concentrate is a dry concentrate comprising:
acetic acid, or an agriculturally acceptable salt thereof; wherein:
the concentrate contains an amount (acid equivalent weight) of the acetic acid, or agriculturally acceptable salt thereof, from about 3% to about 30% by weight of the concentrate; and
the concentrate contains an amount (acid equivalent weight) of dicamba, or an agriculturally acceptable salt or ester thereof, from about 50% to about 80% by weight of the concentrate; and
wherein the sum of the acetic acid weight percent and the dicamba weight percent is less than or equal to 100%.

33. The herbicidal composition concentrate of claim 1, wherein the concentrate is a dry concentrate comprising:
acetic acid, or an agriculturally acceptable salt thereof; and
wherein:
the concentrate contains an amount (acid equivalent weight) of the acetic acid, or agriculturally acceptable salt thereof, from about 5% to about 20% by weight of the concentrate; and
the concentrate contains an amount (acid equivalent weight) of dicamba, or an agriculturally acceptable salt or ester thereof, from about 60% to about 75% by weight of the concentrate.

34. A herbicidal composition concentrate comprising:
(a) dicamba, or an agriculturally acceptable salt or ester thereof;
(b) at least one monocarboxylic acid; and
(c) a neutralizing base, wherein the neutralizing base is an alkali metal hydroxide selected from potassium hydroxide, sodium hydroxide, or a mixture thereof, wherein:
the concentrate comprises an amount of the monocarboxylic acid and neutralizing base sufficient to reduce the concentration of volatilized dicamba in the vapor phase surrounding a diluted version of the concentrate relative to the concentration of volatilized dicamba in the vapor phase surrounding an otherwise identical diluted version of the concentrate lacking the monocarboxylic acid, and neutralizing base.

35. A herbicidal composition comprising:
(a) dicamba or an agriculturally acceptable salt or ester thereof;
(b) at least one monocarboxylic acid, or a monocarboxylate thereof;
(c) a neutralizing base, wherein the neutralizing base is an alkali metal hydroxide selected from potassium hydroxide, sodium hydroxide, or a mixture thereof; and
(d) water;
wherein:
the composition comprises an amount of the monocarboxylic acid and neutralizing base, or an amount of the monocarboxylate, sufficient to reduce the concentration of volatilized dicamba in the vapor phase surrounding the composition relative to the concentration of volatilized dicamba in the vapor phase surrounding an otherwise identical composition lacking the monocarboxylic acid and neutralizing base, or monocarboxylate.

36. The herbicidal composition of claim 35, wherein the herbicidal composition is prepared by a process comprising:
mixing the dicamba, or agriculturally acceptable salt or ester thereof, the monocarboxylic acid, and a neutralizing base comprising an alkali metal hydroxide selected from potassium hydroxide, sodium hydroxide, or a mixture thereof, thereby forming a liquid concentrate comprising the dicamba, or agriculturally salt or ester thereof, and the monocarboxylate.

37. The herbicidal composition of claim 35, wherein the herbicidal composition is prepared by a process comprising:
mixing the dicamba, or agriculturally acceptable salt or ester thereof, with the monocarboxylate, thereby forming a liquid concentrate comprising the dicamba, or agriculturally acceptable salt or ester thereof, and the monocarboxylate.

38. The herbicidal composition of claim 35, wherein:
the molar ratio of monocarboxylic acid, or monocarboxylate thereof, to dicamba, or an agriculturally acceptable salt or ester thereof, is from about 1:10 to about 10:1; and/or
the acid equivalent weight ratio of monocarboxylic acid, or monocarboxylate thereof, to dicamba, or an agriculturally acceptable salt or ester thereof, is from about 1:10 to about 5:1; and/or
the composition comprises an amount (acid equivalent weight) of the monocarboxylic acid, or monocarboxylate thereof, from about 0.01% to about 25% by weight of the composition; and/or the concentration of the monocarboxylic acid, or monocarboxylate thereof, is from about 1 gram (acid equivalent weight)/L to about 250 grams (acid equivalent weight)/L.

39. The herbicidal composition of claim 35, wherein the concentration of dicamba, or an agriculturally acceptable salt or ester thereof, is from about 0.1 grams (acid equivalent weight)/L to about 50 grams (acid equivalent weight)/L.

40. The herbicidal composition of claim 35, wherein the concentration of dicamba, or an agriculturally acceptable salt or ester thereof, is from about 10 grams (acid equivalent weight)/L to about 50 grams (acid equivalent weight)/L.

41. The herbicidal composition of claim 35, wherein the composition comprises an amount (acid equivalent weight) of the monocarboxylic acid, or monocarboxylate thereof, from about 0.05% to about 5% by weight of the composition.

42. The herbicidal composition of claim 35, wherein the neutralizing base is potassium hydroxide.

43. The herbicidal composition of claim 35, wherein the neutralizing base is sodium hydroxide.

44. The herbicidal composition of claim 35, comprising the neutralizing base and monocarboxylic acid at a molar ratio of about 50:50 (1:1) or about 60:40 (1.5:1).

45. The herbicidal composition of claim 35, wherein the composition has a pH equal to or higher than the acid dissociation constant (pKa) of the monocarboxylic acid present in the composition.

* * * * *